United States Patent
Imada et al.

(10) Patent No.: US 11,487,204 B2
(45) Date of Patent: Nov. 1, 2022

(54) RESIST MATERIAL

(71) Applicant: DIC Corporation, Tokyo (JP)

(72) Inventors: Tomoyuki Imada, Ichihara (JP); Shinya Yamamoto, Sakura (JP); Masanori Miyamoto, Sakura (JP)

(73) Assignee: DIC Corporation, Tokyo (JP)

( * ) Notice: Subject to any disclaimer, the term of this patent is extended or adjusted under 35 U.S.C. 154(b) by 19 days.

(21) Appl. No.: 16/630,517

(22) PCT Filed: Jul. 3, 2018

(86) PCT No.: PCT/JP2018/025164
§ 371 (c)(1),
(2) Date: Jan. 13, 2020

(87) PCT Pub. No.: WO2019/021758
PCT Pub. Date: Jan. 31, 2019

(65) Prior Publication Data
US 2020/0166838 A1 May 28, 2020

(30) Foreign Application Priority Data
Jul. 27, 2017 (JP) .............................. JP2017-145464

(51) Int. Cl.
G03F 7/038 (2006.01)
G03F 7/004 (2006.01)
C07C 323/16 (2006.01)
G03F 7/023 (2006.01)

(52) U.S. Cl.
CPC .......... G03F 7/0388 (2013.01); C07C 323/16 (2013.01); G03F 7/0048 (2013.01); G03F 7/0236 (2013.01); G03F 7/0233 (2013.01)

(58) Field of Classification Search
CPC ....... G03F 7/0388; G03F 7/0048; G03F 7/038
See application file for complete search history.

(56) References Cited

U.S. PATENT DOCUMENTS

| 6,093,517 | A * | 7/2000 | Ito | G03F 7/039 562/466 |
| 8,829,247 | B2 * | 9/2014 | Hayashi | C08G 8/04 568/717 |
| 8,969,629 | B2 * | 3/2015 | Takasuka | C07C 43/23 568/722 |
| 9,182,666 | B2 * | 11/2015 | Echigo | C07C 69/54 |
| 9,400,429 | B2 * | 7/2016 | Toyokawa | G03F 7/40 |
| 2011/0111339 | A1 * | 5/2011 | Cheng | G03F 7/095 430/325 |
| 2012/0171615 | A1 * | 7/2012 | Echigo | G03F 7/0382 430/281.1 |
| 2013/0122423 | A1 * | 5/2013 | Echigo | C07C 69/76 430/326 |
| 2013/0157195 | A1 * | 6/2013 | Green | C07C 69/753 430/281.1 |
| 2015/0072274 | A1 * | 3/2015 | Tsuchimura | G03F 7/30 430/5 |
| 2016/0124303 | A1 * | 5/2016 | Takasuka | G03F 7/0395 430/281.1 |
| 2016/0159962 | A1 * | 6/2016 | Imada | G03F 7/0236 430/270.1 |
| 2017/0066703 | A1 * | 3/2017 | Imada | G03F 7/168 |
| 2017/0137556 | A1 * | 5/2017 | Imada | C07C 37/115 |
| 2017/0329226 | A1 * | 11/2017 | Imada | G03F 7/0045 |
| 2017/0334817 | A1 * | 11/2017 | Imada | G03F 7/039 |
| 2017/0349690 | A1 * | 12/2017 | Imada | C07C 39/14 |
| 2019/0276421 | A1 | 9/2019 | Yamamoto et al. | |

FOREIGN PATENT DOCUMENTS

| JP | 200418421 A * | 1/2004 | ............ C07C 69/54 |
| JP | 2010-250256 A | 11/2010 | |
| WO | 2018/101057 A1 | 6/2018 | |

OTHER PUBLICATIONS

International Search Report dated Oct. 2, 2018, issued for PCT/JP2018/025164.

* cited by examiner

*Primary Examiner* — John S Chu
(74) *Attorney, Agent, or Firm* — Locke Lord LLP

(57) ABSTRACT

To provide a resist material that can form a film with high smoothness and uniformity and has high patterning performance, such as resolution, a resist material is provided that contains a calixarene compound (A) with a molecular structure represented by the following structural formula (1) and a resin component (B);

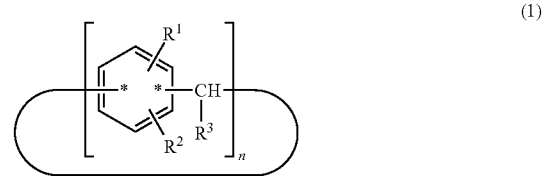

(1)

wherein $R^1$ denotes a perfluoroalkyl group or a structural moiety with a perfluoroalkyl group; $R^2$ denotes a hydrogen atom, a polar group, a polymerizable group, or a structural moiety with a polar group or a polymerizable group; $R^3$ denotes a hydrogen atom, an aliphatic hydrocarbon group that optionally has a substituent, or an aryl group that optionally has a substituent; n denotes an integer in the range of 2 to 10; and * denotes a bonding point with an aromatic ring.

12 Claims, No Drawings

RESIST MATERIAL

TECHNICAL FIELD

The present invention relates to a resist material that can form a film with high smoothness and uniformity and has high patterning performance, such as resolution.

BACKGROUND ART

Due to a decrease in the size of resist patterns in the field of photoresist, there is a growing demand for resist films with higher smoothness and uniformity. Also in the field of color resist, to improve color development and uniformity of quality, there is a growing demand for films with higher smoothness and uniformity. It is generally believed that the addition of fluorinated or silicone surfactants are effective in improving the smoothness of films.

One known fluorinated surfactant for use in color resist applications is a reaction product between a copolymer of a polyoxyperfluoroalkylenediol diacrylate and hydroxyethyl methacrylate and 2-acryloyloxyethyl isocyanate (see PTL 1). However, a relatively large amount of fluorinated surfactant described in PTL 1 is required to achieve desired performance, and the addition of the fluorinated surfactant to a photoresist material disadvantageously reduces resolution.

CITATION LIST

Patent Literature

PTL 1: Japanese Unexamined Patent Application Publication No. 2010-250256

SUMMARY OF INVENTION

Technical Problem

Accordingly, it is an object of the present invention to provide a resist material that can form a film with high smoothness and uniformity and has high patterning performance, such as resolution.

Solution to Problem

As a result of extensive studies to solve the above problems, the present inventors have completed the present invention by finding that a calixarene compound with a perfluoroalkyl group is a surface lubricating agent or a surface leveling agent with very high performance for films, and the addition of the calixarene compound to resist materials does not impair patterning performance, such as resolution.

Thus, the present invention relates to a resist material that contains a calixarene compound (A) with a molecular structure represented by the following structural formula (1) and a resin component (B).

[Chem. 1]

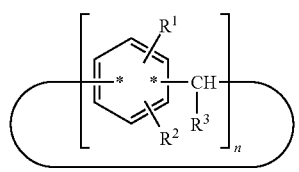

(1)

(wherein $R^1$ denotes a perfluoroalkyl group or a structural moiety with a perfluoroalkyl group; $R^2$ denotes a hydrogen atom, a polar group, a polymerizable group, or a structural moiety with a polar group or a polymerizable group; $R^3$ denotes a hydrogen atom, an aliphatic hydrocarbon group that optionally has a substituent, or an aryl group that optionally has a substituent; n denotes an integer in the range of 2 to 10; and * denotes a bonding point with an aromatic ring.)

Advantageous Effects of Invention

The present invention can provide a resist material that can form a film with high smoothness and uniformity and has high patterning performance, such as resolution.

DESCRIPTION OF EMBODIMENTS

The present invention is described in detail below.

A resist material according to the present invention contains a calixarene compound (A) with a molecular structure represented by the following structural formula (1) and a resin component (B) as essential components.

[Chem. 2]

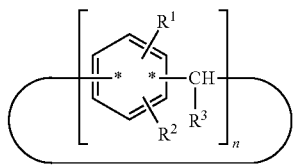

(1)

(wherein $R^1$ denotes a perfluoroalkyl group or a structural moiety with a perfluoroalkyl group; $R^2$ denotes a hydrogen atom, a polar group, a polymerizable group, or a structural moiety with a polar group or a polymerizable group; $R^3$ denotes a hydrogen atom, an aliphatic hydrocarbon group that optionally has a substituent, or an aryl group that optionally has a substituent; n denotes an integer in the range of 2 to 10; and * denotes a bonding point with an aromatic ring.)

The calixarene compound (A) is described below.

Because the calixarene compound (A) has a ring structure, the perfluoroalkyl group is distributed at a higher density than in typical surface lubricating agents of the linear polymer type. Thus, a resist material according to the present invention has much higher surface smoothness and uniformity than resist materials containing typical surface lubricating agents of the linear polymer type. The structural formula (1) may have any binding position of $R^1$ and $R^2$, may have any position of the bonding point represented by *, and may have any structure. In particular, one with a molecular structure represented by the following structural formula (1-1) or (1-2) is preferred because such a calixarene compound (A) has higher performance as a surface lubricating agent.

[Chem. 3]

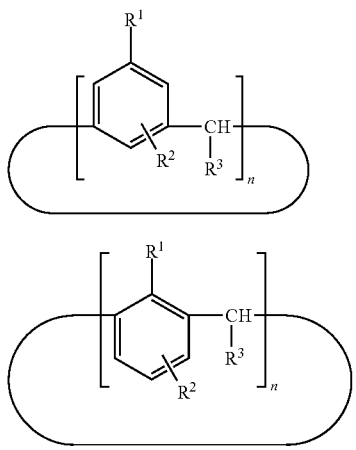

(wherein $R^1$ denotes a perfluoroalkyl group or a structural moiety with a perfluoroalkyl group; $R^2$ denotes a hydrogen atom, a polar group, a polymerizable group, or a structural moiety with a polar group or a polymerizable group; $R^3$ denotes a hydrogen atom, an aliphatic hydrocarbon group that optionally has a substituent, or an aryl group that optionally has a substituent; and n denotes an integer in the range of 2 to 10.)

In the structural formula (1), n denotes an integer in the range of 2 to 10. In particular, n preferably denotes 4, 6, or 8 in terms of structural stability.

$R^1$ in the structural formula (1) denotes a perfluoroalkyl group or a structural moiety with a perfluoroalkyl group and contributes to high surface smoothness and uniformity of films. Although the number of carbon atoms in the perfluoroalkyl group is not particularly limited, the number of carbon atoms preferably ranges from 1 to 6 from the perspective of biological safety. When $R^1$ denotes a structural moiety with a perfluoroalkyl group, the structural moiety except the perfluoroalkyl group is not particularly limited and may have any structure. For example, a specific structure of the structural moiety with a perfluoroalkyl group is represented by —X—RF, wherein RF denotes the perfluoroalkyl group.

For example, X is an alkylene group that optionally has a substituent, a (poly)alkylene ether structure, a (poly)alkylene thioether structure, a (poly)ester structure, a (poly)urethane structure, or a structural moiety composed thereof. Among these, a (poly)alkylene ether chain or a (poly)alkylene thioether chain is preferred, and a structural moiety represented by the following structural formula (2) is more preferred.

[Chem. 4]

$$—R^4—Y—R^4—R^F \qquad (2)$$

(wherein $R^4$ independently denotes an alkylene group having 1 to 6 carbon atoms, RF denotes a perfluoroalkyl group, and Y denotes a hydrogen atom or a sulfur atom.)

$R^4$ in the structural formula (2) independently denotes an alkylene group having 1 to 6 carbon atoms. The alkylene group may be of a straight-chain type or may have a branched structure. The alkylene group is preferably of a straight-chain type because such a calixarene compound (A) has high performance as a surface lubricating agent.

$R^2$ in the structural formula (1) denotes a hydrogen atom, a polar group, a polymerizable group, or a structural moiety with a polar group or a polymerizable group. As described above, although the substitution position of $R^2$ on the aromatic ring is not particularly limited, when $R^2$ denotes a polar group, a polymerizable group, or a structural moiety with a polar group or a polymerizable group, the substitution position on the aromatic ring is preferably a para position relative to $R^1$. $R^2$ located at a para position relative to $R^1$, which contributes to high surface smoothness and uniformity of films, functions as a group with high affinity for a coating substrate or for the resin component (B) or reacts with the resin component (B), thus resulting in a calixarene compound (A) with higher performance as a surface lubricating agent.

Examples of the polar group include a hydroxy group, an amino group, a carboxy group, a thiol group, a phosphate group, a phosphonate group, a phosphinate group, a phosphine oxide group, and an alkoxysilyl group. In a structural moiety with such a polar group, the structural moiety except the polar group is not particularly limited and may have any structure. Specific examples of the structural moiety with a polar group are represented by —O—X—P, wherein P denotes the polar group. For example, X is an alkylene group that optionally has a substituent, a (poly)alkylene ether structure, a (poly)alkylene thioether structure, a (poly)ester structure, a (poly)urethane structure, or a structural moiety composed thereof. In particular, X preferably denotes an alkylene group, more preferably an alkylene group having 1 to 6 carbon atoms. Thus, the structural moiety with a polar group is preferably a structural moiety represented by one of the following structural formulae (3-1) to (3-7), for example.

[Chem. 5]

 (3-1)

 (3-2)

 (3-3)

 (3-4)

 (3-5)

 (3-6)

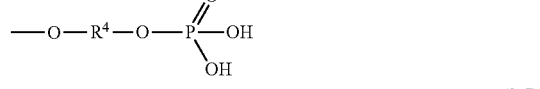 (3-7)

(wherein $R^4$ independently denotes an alkylene group having 1 to 6 carbon atoms, and $R^5$ denotes an alkyl group having 1 to 3 carbon atoms.)

Examples of the polymerizable group include a vinyl group, a vinyloxy group, an ethynyl group, an ethynyloxy group, a (meth)acryloyl group, a (meth)acryloyloxy group, a (2-methyl)glycidyl group, a (2-methyl)glycidyloxy group, a 3-alkyloxetanylmethyl group, and a 3-alkyloxetanylmethyloxy group. In a structural moiety with such a polymerizable group, the structural moiety except the polymerizable group is not particularly limited and may have any structure. Specific examples of the structural moiety with a polymerizable group are represented by —O—X—RP, wherein RP denotes the polymerizable group. For example, X is an alkylene group that optionally has a substituent, a (poly)alkylene ether structure, a (poly)alkylene thioether structure, a (poly)ester structure, a (poly)urethane structure, or a structural moiety composed thereof. The structural moiety with a polymerizable group is preferably a structural moiety represented by one of the following structural formulae (4-1) to (4-8), for example.

[Chem. 6]

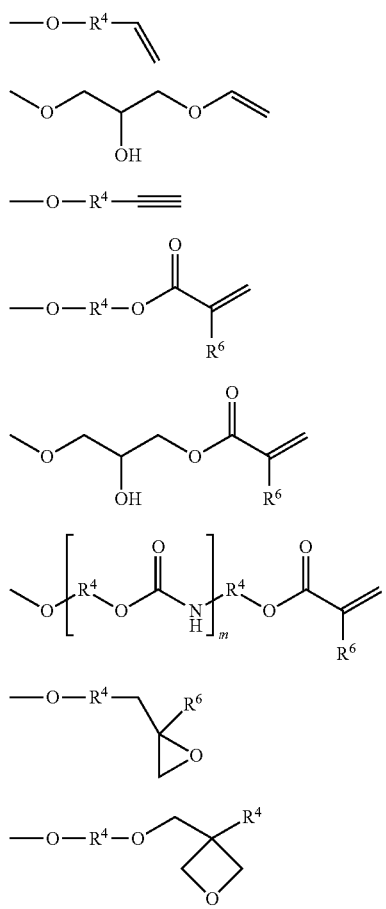

(wherein $R^4$ independently denotes an alkylene group having 1 to 6 carbon atoms, and $R^6$ denotes a hydrogen atom or a methyl group.)

$R^3$ in the structural formula (1) denotes a hydrogen atom, an aliphatic hydrocarbon group that optionally has a substituent, or an aryl group that optionally has a substituent. More specifically, $R^3$ may be an aliphatic hydrocarbon group selected from a methyl group, an ethyl group, a propyl group, an isopropyl group, a butyl group, a t-butyl group, a pentyl group, a hexyl group, a cyclohexyl group, a heptyl group, an octyl group, a nonyl group, and other alkyl groups, or a structural moiety in which one or more hydrogen atoms of these aliphatic hydrocarbon groups are substituted with a hydroxy group, an alkoxy group, a halogen atom, or the like; or a hydrocarbon group with an aromatic ring, such as a phenyl group, a tolyl group, a xylyl group, a naphthyl group, or an anthryl group, or a structural moiety that has a substituent, such as a hydroxy group, an alkyl group, an alkoxy group, or a halogen atom, on these aromatic nuclei. In particular, $R^3$ preferably denotes a hydrogen atom.

The calixarene compound (A) may be produced by any method. A method for producing the calixarene compound (A) is described below. For example, the calixarene compound (A) can be produced by a method including a step of allowing an intermediate (I) represented by the following structural formula (5) to react with a halogenated allyl for allyl etherification (step 1), a step of transferring an allyl group by heating and stirring in the presence of an excessive amount of amine compound to produce an intermediate (II) represented by the following structural formula (6) (step 2), a step of introducing a perfluoroalkyl group (step 3), and, if necessary, a step of introducing a functional group corresponding to $R^2$ (step 4).

[Chem. 7]

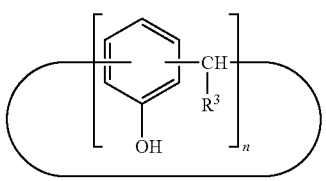

(5)

(wherein $R^3$ denotes a hydrogen atom, an aliphatic hydrocarbon group that optionally has a substituent, or an aryl group that optionally has a substituent; and n denotes an integer in the range of 2 to 10.)

[Chem. 8]

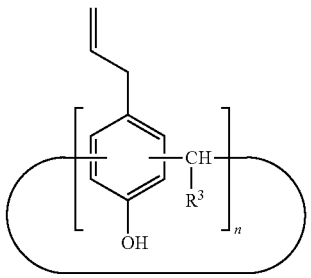

(6)

(wherein $R^3$ denotes a hydrogen atom, an aliphatic hydrocarbon group that optionally has a substituent, or an aryl group that optionally has a substituent; and n denotes an integer in the range of 2 to 10.)

The intermediate (I) represented by the structural formula (5) can be produced by a direct production method from phenol and an aldehyde compound or by a method of reacting a para-alkylphenol with an aldehyde compound to produce an intermediate (a) with a calixarene structure followed by a dealkylation reaction in the presence of phenol and aluminum chloride. In particular, the intermediate (I) can preferably be produced in high yield by reacting a para-alkylphenol with an aldehyde compound to produce an intermediate (a) with a calixarene structure followed by a dealkylation reaction in the presence of phenol and aluminum chloride.

The para-alkylphenol may be any phenol compound with an alkyl group at a para position. The alkyl group may be a methyl group, an ethyl group, a propyl group, a butyl group, a pentyl group, a hexyl group, a heptyl group, an octyl group, or a nonyl group, and is preferably a bulky group, such as a tert-butyl group, to produce the intermediate (a) in higher yield.

The aldehyde compound may be any compound that can cause a condensation reaction with the para-alkylphenol to form a calixarene structure, for example, formaldehyde, an aliphatic aldehyde compound, such as acetaldehyde or propionaldehyde, or an aromatic aldehyde compound, such as benzaldehyde or naphthaldehyde. These may be used alone or in combination. Among these, formaldehyde is preferably used due to its high reactivity. Formaldehyde may be used as an aqueous solution, formalin, or as a solid, paraformaldehyde.

For example, the reaction between the para-alkylphenol and the aldehyde compound can be performed in the presence of an acid or base catalyst at a temperature in the range of approximately 80° C. to 250° C. After the completion of the reaction, the product is preferably washed with water to produce an intermediate (a) of high purity.

As for the reaction ratio of the para-alkylphenol to the aldehyde compound, 0.6 to 2 moles of the aldehyde compound per mole of the para-alkylphenol is preferred to produce the intermediate (a) in high yield.

For example, the acid catalyst is an inorganic acid, such as hydrochloric acid, sulfuric acid, or phosphoric acid, an organic acid, such as methanesulfonic acid, para-toluenesulfonic acid, or oxalic acid, or a Lewis acid, such as boron trifluoride, anhydrous aluminum chloride, or zinc chloride. These may be used alone or in combination. The amount of acid catalyst to be added preferably ranges from 0.05 to 10 parts by mass per 100 parts by mass of the para-alkylphenol and the aldehyde compound in total.

The base catalyst may be any catalyst that acts as a catalyst, for example, an alkali metal hydroxide, such as sodium hydroxide, potassium hydroxide, or rubidium hydroxide, or an alkali metal carbonate, such as sodium carbonate or potassium carbonate. These may be used alone or in combination. The amount of base catalyst to be added preferably ranges from 0.01 to 1 part by mass per 100 parts by mass of the para-alkylphenol and the aldehyde compound in total.

The reaction between the para-alkylphenol and the aldehyde compound may be performed in an organic solvent. Examples of the organic solvent include ester solvents, such as ethyl acetate, methyl acetate, butyl acetate, methyl lactate, ethyl lactate, and butyl lactate; ketone solvents, such as acetone, methyl ethyl ketone, methyl isobutyl ketone, diacetone alcohol, and cyclohexane; alcohol solvents, such as methanol, ethanol, n-propanol, isopropanol, n-butanol, isobutanol, t-butanol, and ethylhexanol; ether solvents, such as dimethyl ether, diethyl ether, isopropyl ether, methyl cellosolve, cellosolve, butyl cellosolve, THF, dioxane, butyl carbitol, and biphenyl ether; and alcohol ether solvents, such as methoxyethanol, ethoxyethanol, and butoxyethanol. These may be used alone or in combination.

Dealkylation of the intermediate (a) can be performed, for example, by a method including adding the intermediate (a) and phenol to an organic solvent that is a poor solvent for the intermediate (a) and a good solvent for phenol, adding aluminum chloride to the organic solvent, and stirring the organic solvent. The reaction is preferably performed in an ice bath or at approximately room temperature.

The amount of phenol to be added preferably ranges from 1 to 2 moles per mole of the hydroxy group in the intermediate (a). The amount of aluminum chloride to be added preferably ranges from 1 to 2 moles per mole of the hydroxy group in the intermediate (a).

The organic solvent may be an aromatic hydrocarbon solvent, for example, benzene or an alkylbenzene, such as toluene or xylene.

After the completion of the reaction, the product is preferably purified by washing with water or by reprecipitation to produce an intermediate (I) of high purity.

The step of allowing the intermediate (I) to react with a halogenated allyl for allyl etherification (step 1) can be performed, for example, in the same manner as so-called Williamson ether synthesis, by stirring the intermediate (I) and the halogenated allyl in the presence of a basic catalyst at approximately room temperature. The reaction may be performed in an organic solvent. In particular, the reaction proceeds efficiently in a polar solvent, such as N-dimethylformamide, N-dimethylacetamide, or tetrahydrofuran. After the completion of the reaction, the product is preferably purified by washing with an alcohol solvent or the like.

In the step 2 after the step 1, the allyl etherification product in the step 1 is heated with stirring in the presence of an excessive amount of amine compound to transfer the allyl group, thereby producing the intermediate (II) represented by the structural formula (6).

Examples of the amine compound include tertiary amines, such as N,N-dimethylaniline, N,N-diethylaniline, N,N,N-trimethylamine, N,N,N-triethylamine, and diisopropylethylamine, and secondary amines, such as N,N-dimethylamine and N,N-diethylamine. These may be used alone or in combination.

After the completion of the reaction, the product is preferably purified by washing with an alcohol solvent or the like.

In the step 3, a perfluoroalkyl group is introduced into the intermediate (II) prepared in the step 2. Any perfluoroalkyl group introducing agent may be used that can react with the allyl group of the intermediate (II) to introduce a perfluoroalkyl group. A thiol compound with a perfluoroalkyl group has particularly high reactivity.

For example, the thiol compound is represented by the following structural formula (7).

[Chem. 9]

(wherein $R^4$ denotes an alkylene group having 1 to 6 carbon atoms, and RF denotes a perfluoroalkyl group.)

The thiol compounds may be used alone or in combination. The amount of thiol compound to be added is preferably excessively larger than the amount of the allyl group of the intermediate (II) and more preferably ranges from approximately 1 to 5 moles per mole of the allyl group.

For example, the reaction between the intermediate (II) and the thiol compound can be performed in the presence of a catalyst at a temperature in the range of approximately 50° C. to 80° C. The reaction may be performed in an organic solvent. Examples of the organic solvent include aromatic hydrocarbon solvents, such as toluene and xylene; alcohol solvents, such as methanol, ethanol, and isopropanol; and ketone solvents, such as methyl isobutyl ketone and methyl ethyl ketone.

The catalyst is 2,2'-azobis(2,4-dimethylvaleronitrile), for example. The amount of catalyst to be added preferably ranges from 0.05 to 0.5 moles per mole of the allyl group of the intermediate (II).

After the completion of the reaction, the product is preferably purified by washing with water or by reprecipitation.

The step 4 is performed to introduce a functional group corresponding to $R^2$ in the case that a compound represented by the structural formula (1) in which $R^2$ denotes a polar group, a polymerizable group, or a structural moiety with a polar group or a polymerizable group is produced. Any functional group introducing agent that can react with a phenolic hydroxy group may be used. In general, the target compound can efficiently be produced by a method of reacting a halide having a structural moiety corresponding to $R^2$ in the presence of a basic catalyst in the same manner as so-called Williamson ether synthesis.

The resin component (B) is described below.

The resin component (B) may have any structure or may be of any resin type and may be any resin material that can be utilized for resist applications. Although resin materials widely used in resist applications are described below as examples of the resin component (B), the resin component (B) is not limited to these resin materials because the calixarene compound (A) has very high performance as a surface lubricating agent or as a surface leveling agent for films even when the calixarene compound (A) is added to any resin material.

For example, the resin component (B) is an active energy beam curing compound (B1), a resin with a novolak phenolic hydroxy group or a modified product thereof (B2), a calixarene compound other than the calixarene compound (A) or a modified product thereof (B3), a (poly)vinyl resin or a modified product thereof (B4), or another resin with a phenolic hydroxy group or a modified product thereof (B5).

For example, the active energy beam curing compound (B1) is a compound with a (meth)acryloyl group. For example, the compound with a (meth)acryloyl group is a mono(meth)acrylate compound or a modified product thereof (B1-1), an aliphatic hydrocarbon type poly(meth) acrylate compound or a modified product thereof (B1-2), an alicyclic poly(meth)acrylate compound or a modified product thereof (B1-3), an aromatic poly(meth)acrylate compound or a modified product thereof (B1-4), a (meth)acrylate resin with a silicone chain or a modified product thereof (B1-5), an epoxy (meth)acrylate resin or a modified product thereof (B1-6), a urethane (meth)acrylate resin or a modified product thereof (B1-7), an acrylic (meth)acrylate resin or a modified product thereof (B1-8), or a dendrimer type (meth) acrylate resin or a modified product thereof (B1-9).

For example, the mono(meth)acrylate compound or a modified product thereof (B1-1) is an aliphatic mono(meth) acrylate compound, such as methyl (meth)acrylate, ethyl (meth)acrylate, hydroxyethyl (meth)acrylate, propyl (meth) acrylate, hydroxypropyl (meth)acrylate, butyl (meth)acrylate, or 2-ethylhexyl (meth)acrylate; an alicyclic mono (meth)acrylate compound, such as cyclohexyl (meth) acrylate, isobornyl (meth)acrylate, or adamantyl mono (meth)acrylate; a heterocyclic mono(meth)acrylate compound, such as glycidyl (meth)acrylate or tetrahydrofurfuryl acrylate; an aromatic mono(meth)acrylate compound, such as phenyl (meth)acrylate, benzyl (meth)acrylate, phenoxy (meth)acrylate, phenoxyethyl (meth)acrylate, phenoxyethoxyethyl (meth)acrylate, 2-hydroxy-3-phenoxypropyl (meth)acrylate, phenylphenol (meth)acrylate, phenylbenzyl (meth)acrylate, phenoxybenzyl (meth)acrylate, benzylbenzyl (meth)acrylate, phenylphenoxyethyl (meth) acrylate, or para-cumylphenol (meth)acrylate; a mono (meth)acrylate compound, such as a compound represented by the following structural formula (8); a (poly)oxyalkylene-modified product having a (poly)oxyalkylene chain, such as a (poly)oxyethylene chain, a (poly)oxypropylene chain, or a (poly)oxytetramethylene chain, in a molecular structure of the above mono(meth)acrylate compound; or a lactone-modified product having a (poly)lactone structure in a molecular structure of the above mono(meth)acrylate compound.

[Chem. 10]

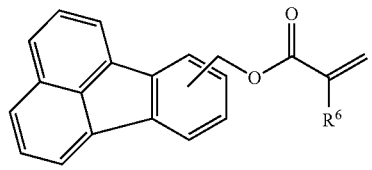

(8)

(wherein $R^6$ denotes a hydrogen atom or a methyl group.)

For example, the aliphatic hydrocarbon type poly(meth) acrylate compound or a modified product thereof (B1-2) is an aliphatic di(meth)acrylate compound, such as ethylene glycol di(meth)acrylate, propylene glycol di(meth)acrylate, butanediol di(meth)acrylate, hexanediol di(meth)acrylate, or neopentyl glycol di(meth)acrylate; an aliphatic tri(meth) acrylate compound, such as trimethylolpropane tri(meth) acrylate, glycerin tri(meth)acrylate, pentaerythritol tri(meth) acrylate, ditrimethylolpropane tri(meth)acrylate, or dipentaerythritol tri(meth)acrylate; a tetra or higher functional aliphatic poly(meth)acrylate compound, such as pentaerythritol tetra(meth)acrylate, ditrimethylolpropane tetra (meth)acrylate, dipentaerythritol tetra(meth)acrylate, dipentaerythritol penta(meth)acrylate, or dipentaerythritol hexa(meth)acrylate; a (poly) oxyalkylene-modified product having a (poly)oxyalkylene chain, such as a (poly)oxyethylene chain, a (poly)oxypropylene chain, or a (poly)oxytetramethylene chain, in a molecular structure of the above aliphatic hydrocarbon type poly(meth)acrylate compound; or a lactone-modified product having a (poly)lactone structure in a molecular structure of the above aliphatic hydrocarbon type poly(meth)acrylate compound.

For example, the alicyclic poly(meth)acrylate compound or a modified product thereof (B1-3) is an alicyclic di(meth) acrylate compound, such as 1,4-cyclohexanedimethanol di(meth)acrylate, norbornane di(meth)acrylate, norbornane dimethanol di(meth)acrylate, dicyclopentanyl di(meth)acrylate, or tricyclodecane dimethanol di(meth)acrylate; a (poly) oxyalkylene-modified product having a (poly)oxyalkylene chain, such as a (poly)oxyethylene chain, a (poly)oxypropylene chain, or a (poly)oxytetramethylene chain, in a molecular structure of the above alicyclic poly(meth)acrylate compound; or a lactone-modified product having a (poly)lactone structure in a molecular structure of the above alicyclic poly(meth)acrylate compound.

For example, the aromatic poly(meth)acrylate compound or a modified product thereof (B1-4) is an aromatic di(meth) acrylate compound, such as biphenol di(meth)acrylate, bisphenol di(meth)acrylate, bicarbazole compounds represented by the following structural formula (9), or a fluorene compound represented by the following structural formula (10-1) or (10-2); a (poly)oxyalkylene-modified product having a (poly)oxyalkylene chain, such as a (poly)oxyethylene chain, a (poly)oxypropylene chain, or a (poly)oxytetramethylene chain, in a molecular structure of the above aromatic poly(meth)acrylate compound; or a lactone-modified product having a (poly)lactone structure in a molecular structure of the above aromatic poly(meth)acrylate compound.

[Chem. 11]

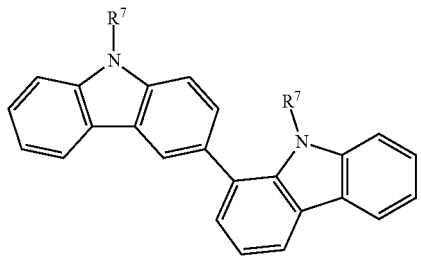

(9)

[wherein $R^7$ independently denotes a (meth)acryloyl group, a (meth)acryloyloxy group, or a (meth)acryloyloxyalkyl group.]

[Chem. 12]

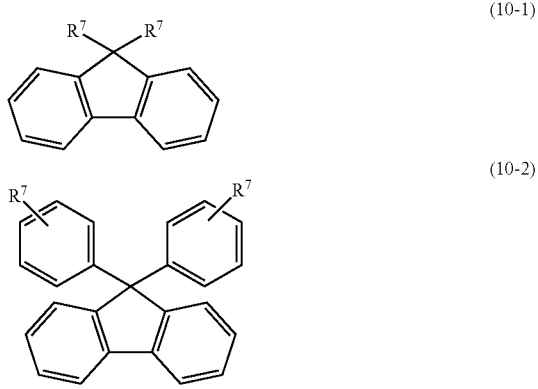

(10-1)

(10-2)

[wherein $R^7$ independently denotes a (meth)acryloyl group, a (meth)acryloyloxy group, or a (meth)acryloyloxyalkyl group.]

The (meth)acrylate resin with a silicone chain or a modified product thereof (B1-5) may be any compound having a silicone chain and a (meth)acryloyl group in its molecular structure and may be produced by any method. More specifically, the (meth)acrylate resin with a silicone chain or a modified product thereof (R5) may be a reaction product of a silicone compound with an alkoxysilane group and a (meth)acrylate compound with a hydroxy group.

Examples of commercial products of the silicone compound with an alkoxysilane group include "X-40-9246" (alkoxy group content: 12% by mass), "KR-9218" (alkoxy group content: 15% by mass), "X-40-9227" (alkoxy group content: 15% by mass), "KR-510" (alkoxy group content: 17% by mass), "KR-213" (alkoxy group content: 20% by mass), "X-40-9225" (alkoxy group content: 24% by mass), "X-40-9250" (alkoxy group content: 25% by mass), "KR-500" (alkoxy group content: 28% by mass), "KR-401N" (alkoxy group content: 33% by mass), "KR-515" (alkoxy group content: 40% by mass), and "KC-89S" (alkoxy group content: 45% by mass), each manufactured by Shin-Etsu Chemical Co., Ltd. These may be used alone or in combination. In particular, the alkoxy group content preferably ranges from 15% to 40% by mass. When at least two silicone compounds are used in combination, the average alkoxy group content preferably ranges from 15% to 40% by mass.

For example, the (meth)acrylate compound with a hydroxy group is a (meth)acrylate compound with a hydroxy group, such as hydroxyethyl (meth)acrylate, hydroxypropyl (meth)acrylate, trimethylolpropane di(meth)acrylate, pentaerythritol tri(meth)acrylate, ditrimethylolpropane tri(meth)acrylate, or dipentaerythritol penta(meth)acrylate; a (poly)oxyalkylene-modified product having a (poly)oxyalkylene chain, such as a (poly)oxyethylene chain, a (poly)oxypropylene chain, or a (poly)oxytetramethylene chain, in a molecular structure of the above (meth)acrylate compound with a hydroxy group; or a lactone-modified product having a (poly)lactone structure in a molecular structure of the above (meth)acrylate compound with a hydroxy group.

The (meth)acrylate resin with a silicone chain or a modified product thereof (B1-5) may also be a commercial silicone oil having a (meth)acryloyl group on one end, such as "X-22-174ASX" (methacryloyl group equivalent: 900 g/equivalent), "X-22-174BX" (methacryloyl group equivalent: 2,300 g/equivalent), "X-22-174DX" (methacryloyl group equivalent: 4,600 g/equivalent), "KF-2012" (methacryloyl group equivalent: 4,600 g/equivalent), "X-22-2426" (methacryloyl group equivalent: 12,000 g/equivalent), "X-22-2404" (methacryloyl group equivalent: 420 g/equivalent), or "X-22-2475" (methacryloyl group equivalent: 420 g/equivalent), each manufactured by Shin-Etsu Chemical Co., Ltd.; a silicone oil having a (meth)acryloyl group on both ends, such as "X-22-164" (methacryloyl group equivalent: 190 g/equivalent), "X-22-164AS" (methacryloyl group equivalent: 450 g/equivalent), "X-22-164A" (methacryloyl group equivalent: 860 g/equivalent), "X-22-164B" (methacryloyl group equivalent: 1,600 g/equivalent), "X-22-164C" (methacryloyl group equivalent: 2,400 g/equivalent), "X-22-164E" (methacryloyl group equivalent: 3,900 g/equivalent), or "X-22-2445" (acryloyl group equivalent: 1,600 g/equivalent), each manufactured by Shin-Etsu Chemical Co., Ltd.; or an oligomer type silicone compound having a plurality of (meth)acryloyl groups in one molecule, such as "KR-513" (methacryloyl group equivalent: 210 g/equivalent) or "-40-9296" (methacryloyl group equivalent: 230 g/equivalent) each manufactured by Shin-Etsu Chemical Co., Ltd, or "AC-SQ TA-100" (acryloyl group equivalent: 165 g/equivalent), "AC-SQ SI-20" (acryloyl group equivalent: 207 g/equivalent), "MAC-SQ TM-100" (methacryloyl group equivalent: 179 g/equivalent), "MAC-SQ SI-20" (methacryloyl group equivalent: 224 g/equivalent), or "MAC-SQ HDM" (methacryloyl group equivalent: 239 g/equivalent), each manufactured by Toagosei Co., Ltd.

The (meth)acrylate resin with a silicone chain or a modified product thereof (B1-5) preferably has a mass-average molecular mass (Mw) in the range of 1,000 to 10,000, more preferably 1,000 to 5,000. The (meth)acrylate resin with a silicone chain or a modified product thereof (B1-5) preferably has a (meth)acryloyl group equivalent in the range of 150 to 5,000 g/equivalent, more preferably 150 to 2,500 g/equivalent.

In the present invention, the molecular weight and molecular weight distribution of resin were measured with a gel permeation chromatograph (GPC) under the following conditions.

Measuring apparatus: HLC-8220 manufactured by Tosoh Corporation

Column: guard column $H_{XL}$-H manufactured by Tosoh Corporation
+TSKgel G5000HXL manufactured by Tosoh Corporation
+TSKgel G4000HXL manufactured by Tosoh Corporation
+TSKgel G3000HXL manufactured by Tosoh Corporation
+TSKgel G2000HXL manufactured by Tosoh Corporation Detector: differential refractometer (RI)

Data processing: SC-8010 manufactured by Tosoh Corporation

Measurement conditions: Column temperature 40° C.

Solvent tetrahydrofuran

Flow rate 1.0 ml/min

Reference: polystyrene

Sample: A tetrahydrofuran solution with a resin solid content of 0.4% by mass passed through a microfilter (100 μl).

For example, the epoxy (meth)acrylate resin or a modified product thereof (B1-6) is a reaction product of an epoxy resin and a (meth)acrylic acid or its anhydride. For example, the epoxy resin is a diglycidyl ether of a divalent phenol, such as hydroquinone or catechol; a diglycidyl ether of a biphenol compound, such as 3,3'-biphenyldiol or 4,4'-biphenyldiol; a bisphenol epoxy resin, such as a bisphenol A epoxy resin, a bisphenol B epoxy resin, a bisphenol F epoxy resin, or a bisphenol S epoxy resin; a polyglycidyl ether of a naphthol compound, such as 1,4-naphthalenediol, 1,5-naphthalenediol, 1,6-naphthalenediol, 2,6-naphthalenediol, 2,7-naphthalenediol, binaphthol, or bis(2,7-dihydroxynaphthyl)methane; a triglycidyl ether, such as 4,4',4"-methylidynetrisphenol; a novolak epoxy resin, such as a phenol novolak epoxy resin or a cresol novolak resin; a (poly)oxyalkylene-modified product having a (poly)oxyalkylene chain, such as a (poly)oxyethylene chain, a (poly)oxypropylene chain, or a (poly)oxytetramethylene chain, in a molecular structure of the above epoxy resin; or a lactone-modified product having a (poly)lactone structure in a molecular structure of the above epoxy resin. The epoxy (meth)acrylate resin or a modified product thereof (B1-6) may be produced by introducing a carboxy group through a reaction between a hydroxy group in the molecular structure and a polycarboxylic anhydride. Examples of the polycarboxylic anhydride include acid anhydrides of oxalic acid, malonic acid, succinic acid, glutaric acid, adipic acid, pimelic acid, suberic acid, azelaic acid, sebacic acid, maleic acid, fumaric acid, phthalic acid, isophthalic acid, terephthalic acid, tetrahydrophthalic acid, hexahydrophthalic acid, and methylhexahydrophthalic acid.

For example, the urethane (meth)acrylate resin or a modified product thereof (B1-7) is a reaction product of a polyisocyanate compound, a (meth)acrylate compound with a hydroxy group, and if necessary a polyol compound. Examples of the polyisocyanate compound include aliphatic diisocyanate compounds, such as butane diisocyanate, hexamethylene diisocyanate, 2,2,4-trimethylhexamethylene diisocyanate, and 2,4,4-trimethylhexamethylene diisocyanate; alicyclic diisocyanate compounds, such as norbornane diisocyanate, isophorone diisocyanate, hydrogenated xylylene diisocyanate, and hydrogenated diphenylmethane diisocyanate; aromatic diisocyanate compounds, such as tolylene diisocyanate, xylylene diisocyanate, tetramethylxylylene diisocyanate, diphenylmethane diisocyanate, and 1,5-naphthalene diisocyanate; polymethylene polyphenyl polyisocyanates with a repeating structure represented by the following structural formula (11); and isocyanurate-modified products, biuret-modified products, and allophanate-modified products thereof.

[Chem. 13]

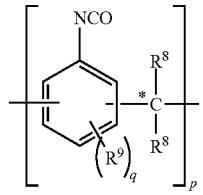

(11)

[wherein $R^8$ independently denotes a hydrogen atom or a hydrocarbon group having 1 to 6 carbon atoms, $R^9$ independently denotes an alkyl group having 1 to 4 carbon atoms or a bonding point to be bonded to a structural moiety represented by the structural formula (11) via a methylene group marked with *, q denotes an integer of 0 or 1 to 3, and p denotes an integer of 1 or more.]

For example, the (meth)acrylate compound with a hydroxy group is a (meth)acrylate compound with a hydroxy group, such as hydroxyethyl (meth)acrylate, hydroxypropyl (meth)acrylate, trimethylolpropane di(meth)acrylate, pentaerythritol tri(meth)acrylate, ditrimethylolpropane tri(meth)acrylate, or dipentaerythritol penta(meth)acrylate; a (poly)oxyalkylene-modified product having a (poly)oxyalkylene chain, such as a (poly)oxyethylene chain, a (poly)oxypropylene chain, or a (poly)oxytetramethylene chain, in a molecular structure of the above (meth)acrylate compound with a hydroxy group; or a lactone-modified product having a (poly)lactone structure in a molecular structure of the above (meth)acrylate compound with a hydroxy group.

For example, the polyol compound is an aliphatic polyol compound, such as ethylene glycol, propylene glycol, butanediol, hexanediol, glycerin, trimethylolpropane, ditrimethylolpropane, pentaerythritol, or dipentaerythritol; an aromatic polyol compound, such as biphenol or bisphenol; a (poly)oxyalkylene-modified product having a (poly)oxyalkylene chain, such as a (poly)oxyethylene chain, a (poly)oxypropylene chain, or a (poly)oxytetramethylene chain, in a molecular structure of the above polyol compound; or a lactone-modified product having a (poly)lactone structure in a molecular structure of the above polyol compound.

For example, the acrylic (meth)acrylate resin or a modified product thereof (B1-8) is produced by introducing a (meth)acryloyl group into an acrylic resin intermediate produced by polymerization of an essential component, a (meth)acrylate monomer (α) with a reactive functional group, such as a hydroxy group, a carboxy group, an isocyanate group, or a glycidyl group. The (meth)acryloyl group is introduced into the acrylic resin intermediate by reacting the acrylic resin intermediate with a (meth)acrylate monomer (β) with a reactive functional group that can react with the above functional group.

For example, the (meth)acrylate monomer (α) with a reactive functional group is a (meth)acrylate monomer with a hydroxy group, such as hydroxyethyl (meth)acrylate or hydroxypropyl (meth)acrylate; a (meth)acrylate monomer with a carboxy group, such as (meth)acrylic acid; a (meth)acrylate monomer with an isocyanate group, such as 2-acryloyloxyethyl isocyanate, 2-methacryloyloxyethyl isocyanate, or 1,1-bis(acryloyloxymethyl)ethyl isocyanate; or a (meth)acrylate monomer with a glycidyl group, such as glycidyl (meth)acrylate or 4-hydroxybutyl acrylate glycidyl ether. These may be used alone or in combination.

The acrylic resin intermediate may also be produced by polymerization of the (meth)acrylate monomer (α) and if necessary another compound with a polymerizable unsaturated group. Examples of the other compound with a polymerizable unsaturated group include alkyl (meth)acrylates, such as methyl (meth)acrylate, ethyl (meth)acrylate, propyl (meth)acrylate, butyl (meth)acrylate, and 2-ethylhexyl (meth)acrylate; cyclic (meth)acrylates, such as cyclohexyl (meth)acrylate, isobornyl (meth)acrylate, and dicyclopentanyl (meth)acrylate; (meth)acrylates with an aromatic ring, such as phenyl (meth)acrylate, benzyl (meth)acrylate, and phenoxyethyl acrylate; (meth)acrylates with a silyl group, such as 3-methacryloxypropyltrimethoxysilane; and styrene derivatives, such as styrene, α-methylstyrene, and chlorostyrene. These may be used alone or in combination. The ratio of the (meth)acrylate monomer (α) to the other compound with a polymerizable unsaturated group is not particularly limited and depends on desired performance or the like.

The (meth)acrylate monomer (β) may be any (meth)acrylate monomer that can react with the reactive functional group of the (meth)acrylate monomer (α), and the following combinations are preferred in terms of reactivity. When the (meth)acrylate monomer (α) is the (meth)acrylate with a hydroxy group, the (meth)acrylate monomer (β) is preferably a (meth)acrylate with an isocyanate group. When the (meth)acrylate monomer (α) is the (meth)acrylate with a carboxy group, the (meth)acrylate monomer (β) is preferably the (meth)acrylate with a glycidyl group. When the (meth)acrylate monomer (α) is the (meth)acrylate with an isocyanate group, the (meth)acrylate monomer (β) is preferably the (meth)acrylate with a hydroxy group. When the (meth)acrylate monomer (α) is the (meth)acrylate with a glycidyl group, the (meth)acrylate monomer (β) is preferably the (meth)acrylate with a carboxy group. The number of moles of (meth)acrylate monomer (β) to be reacted depends on desired performance or the like. A reactive functional group of the acrylic resin intermediate derived from the (meth)acrylate monomer (α) may remain partly or may react completely with the (meth)acrylate monomer (β). When the acrylic resin intermediate has a hydroxy group in its molecular structure, the hydroxy group may react partly or completely with a polycarboxylic anhydride to introduce a carboxy group. Examples of the polycarboxylic anhydride include acid anhydrides of oxalic acid, malonic acid, succinic acid, glutaric acid, adipic acid, pimelic acid, suberic acid, azelaic acid, sebacic acid, maleic acid, fumaric acid, phthalic acid, isophthalic acid, terephthalic acid, tetrahydrophthalic acid, hexahydrophthalic acid, and methylhexahydrophthalic acid.

The acrylic (meth)acrylate resin or a modified product thereof (B1-8) preferably has a mass-average molecular mass (Mw) in the range of 5,000 to 50,000. The acrylic (meth)acrylate resin or a modified product thereof (B1-8) preferably has a (meth)acryloyl group equivalent in the range of 200 to 300 g/equivalent.

The dendrimer type (meth)acrylate resin or a modified product thereof (B1-9) refers to a resin with a regular multibranched structure and with a (meth)acryloyl group at the end of each branched chain and is also referred to as a hyperbranched or star polymer. Examples of such compounds include, but are not limited to, those represented by the following structural formulae (12-1) to (12-8). Any resins with a regular multibranched structure and with a (meth)acryloyl group at the end of each branched chain may be used.

[Chem. 14]

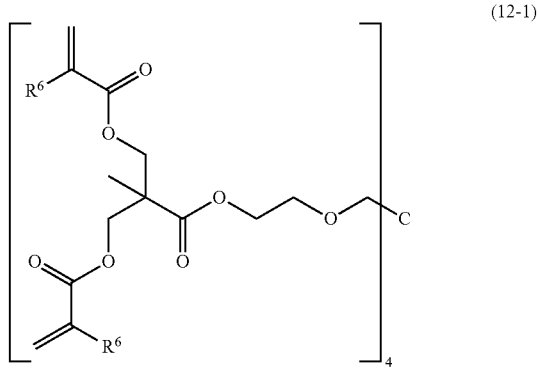

(12-1)

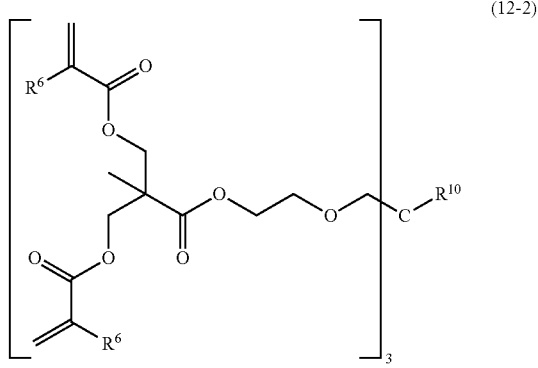

(12-2)

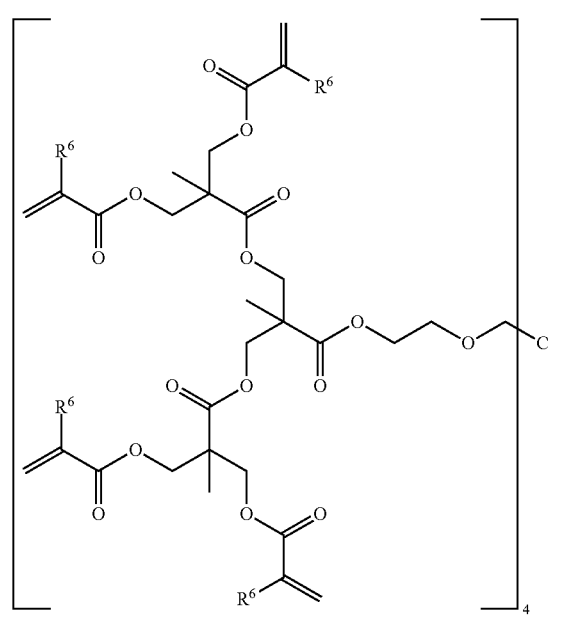

(12-3)

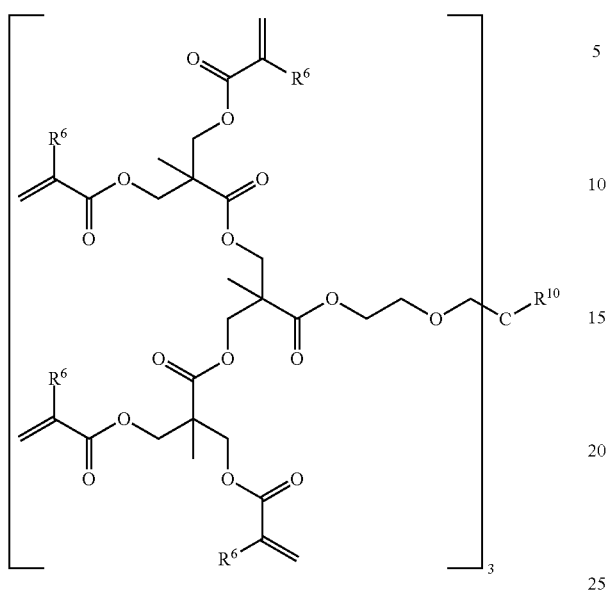 (12-4)

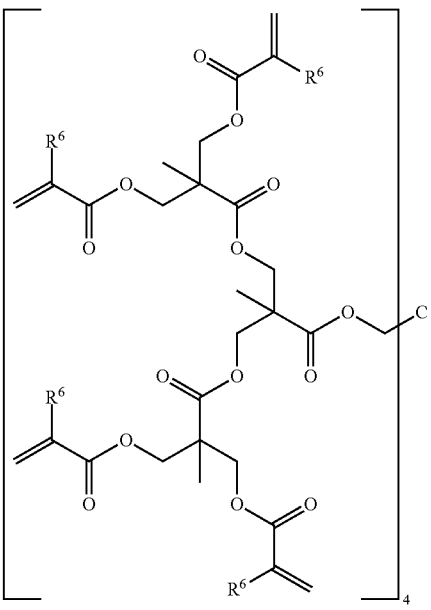 (12-7)

[Chem. 15]

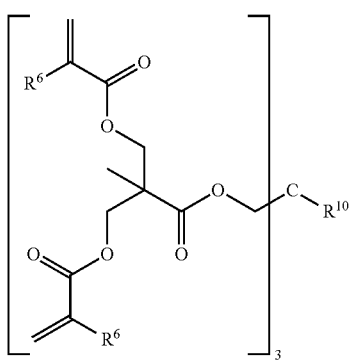 (12-5)

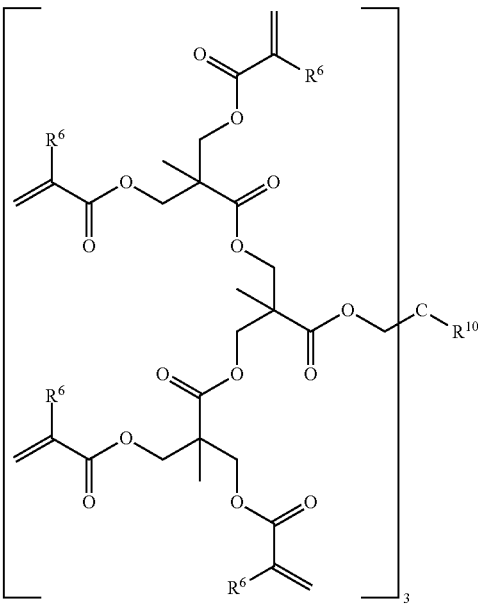 (12-8)

(12-6)

(wherein $R^6$ denotes a hydrogen atom or a methyl group, and $R^{10}$ denotes a hydrocarbon group having 1 to 4 carbon atoms.)

The dendrimer type (meth)acrylate resin or a modified product thereof (B1-9) may be a commercial product, for example, "Viscoat #1000" [mass-average molecular mass (Mw): 1,500 to 2,000, average number of (meth)acryloyl groups per molecule: 14], "Viscoat 1020" [mass-average molecular mass (Mw): 1,000 to 3,000], "SIRIUS 501" [mass-average molecular mass (Mw): 15,000 to 23,000], each manufactured by Osaka Organic Chemical Industry Ltd., "SP-1106" manufactured by MIWON [mass-average molecular mass (Mw): 1,630, average number of (meth)acryloyl groups per molecule: 18], "CN2301", "CN2302" [average number of (meth)acryloyl groups per molecule: 16], "CN2303" [average number of (meth)acryloyl groups per molecule: 6], "CN2304" [average number of (meth)

acryloyl groups per molecule: 18], each manufactured by SARTOMER, "Esdrimer HU-22" manufactured by Nippon Steel & Sumikin Chemical Co., Ltd., "A-HBR-5" manufactured by Shin Nakamura Chemical Co., Ltd., "New Frontier R-1150" manufactured by Dai-ichi Kogyo Seiyaku Co., Ltd., or "Hypertech UR-101" manufactured by Nissan Chemical Industries, Ltd.

The dendrimer type (meth)acrylate resin or a modified product thereof (B1-9) preferably has a mass-average molecular mass (Mw) in the range of 1,000 to 30,000. The average number of (meth)acryloyl groups per molecule preferably ranges from 5 to 30.

In the resin with a novolak phenolic hydroxy group or a modified product thereof (B2), the resin with a novolak phenolic hydroxy group is a polycondensation reaction product between a monomer with a phenolic hydroxy group and an aldehyde compound. Examples of the monomer with a phenolic hydroxy group include monohydroxy compounds, such as phenol, naphthol, and anthracenol, polyhydroxy compounds, such as dihydroxybenzene, dihydroxynaphthalene, biphenol, bisphenol, and tri(hydroxyaryl) alkane, and compounds having a substituent, such as an alkyl group, an alkoxy group, a halogen atom, an aryl group, an amino group, or a nitro group, on these aromatic nuclei. These may be used alone or in combination.

Examples of the aldehyde compound include formaldehyde, aliphatic aldehyde compounds, such as acetaldehyde and propionaldehyde; and aromatic aldehyde compounds, such as benzaldehyde, hydroxybenzaldehyde, naphthaldehyde, and hydroxynaphthaldehyde. Formaldehyde may be used as an aqueous solution, formalin, or as a solid, paraformaldehyde. The aldehyde compounds may be used alone or in combination.

The resin with a novolak phenolic hydroxy group is typically produced by a reaction between the monomer with a phenolic hydroxy group and an aldehyde compound in the presence of an acid catalyst at a temperature in the range of 50° C. to 200° C.

In a modified product of the resin with a novolak phenolic hydroxy group, for example, a hydrogen atom of a hydroxy group of the resin with a novolak phenolic hydroxy group is partly or entirely substituted with an acid dissociable protective group. Examples of the acid dissociable protective group include tertiary alkyl groups, alkoxyalkyl groups, acyl groups, alkoxycarbonyl groups, cyclic hydrocarbon groups containing a heteroatom, and trialkylsilyl groups. Examples of the tertiary alkyl groups include a t-butyl group and a t-pentyl group. Examples of the alkoxyalkyl groups include a methoxyethyl group, an ethoxyethyl group, a propoxyethyl group, a butoxyethyl group, a cyclohexyloxyethyl group, and a phenoxyethyl group. Examples of the acyl groups include an acetyl group, an ethanoyl group, a propanoyl group, a butanoyl group, a cyclohexanecarbonyl group, and a benzoyl group. Examples of the alkoxycarbonyl groups include a methoxycarbonyl group, an ethoxycarbonyl group, a propoxycarbonyl group, a butoxycarbonyl group, a cyclohexyloxycarbonyl group, and a phenoxycarbonyl group. Examples of the cyclic hydrocarbon groups containing a heteroatom include a tetrahydrofuranyl group and a tetrahydropyranyl group. Examples of the trialkylsilyl groups include a trimethylsilyl group, a triethylsilyl group, and a t-butyldimethylsilyl group.

A hydrogen atom of a phenolic hydroxy group is partly or entirely substituted with an acid dissociable protective group, for example, by a reaction between the resin with a novolak phenolic hydroxy group and a protective group introducing agent represented by one of the following structural formulae (13-1) to (13-8.

(13-1)

(13-2)

(13-3)

(13-4)

(13-5)

(13-6)

(13-7)

(13-8)

(wherein X denotes a halogen atom, $R^{11}$ independently denotes an alkyl group having 1 to 6 carbon atoms or a phenyl group, and n is 1 or 2.)

When the protective group introducing agent is a compound represented by one of the structural formulae (13-1), (13-3), (13-4), (13-5), (13-6), and (13-8), for example, the resin with a novolak phenolic hydroxy group is allowed to react with the protective group introducing agent in the presence of a basic catalyst, such as pyridine or triethylamine. When the protective group introducing agent is a compound represented by the structural formula (13-2) or (13-7), for example, the resin with a novolak phenolic hydroxy group is allowed to react with the protective group introducing agent in the presence of an acidic catalyst, such as hydrochloric acid.

The resin with a novolak phenolic hydroxy group or a modified product thereof (B2) preferably has a mass-average molecular mass (Mw) in the range of 3,000 to 50,000. The resin with a novolak phenolic hydroxy group or a modified product thereof (B2) preferably has a molecular weight distribution (Mw/Mn) in the range of 1.1 to 10.

In the calixarene compound or a modified product thereof (B3), the calixarene compound may be produced from a monomer with a phenolic hydroxy group and an aldehyde compound in the same manner as in the resin with a novolak phenolic hydroxy group. Although the preferred conditions for the reaction between the monomer with a phenolic hydroxy group and the aldehyde compound to produce the calixarene compound depend on the types of the compounds, the calixarene compound may be produced by a generally known method. For example, when the monomer with a phenolic hydroxy group is a compound with a benzene skeleton, such as phenol, a substituted phenol, or dihydroxybenzene, 1 mol of the monomer with a phenolic hydroxy group is preferably allowed to react with 0.8 to 1.5 mol of the aldehyde compound in the presence of an alkali metal basic catalyst or an acid catalyst at a temperature in the range of approximately 80° C. to 230° C. When the monomer with a phenolic hydroxy group is a compound with a naphthalene skeleton, such as naphthol, a substituted naphthol, or dihydroxynaphthalene, and the aldehyde compound is formaldehyde, 1 mol of the monomer with a phenolic hydroxy group is preferably allowed to react with 1 to 2 mol of formaldehyde in the presence of an alkali metal basic catalyst at a temperature in the range of approximately 20° C. to 100° C. When the monomer with a phenolic hydroxy group is a compound with a naphthalene skeleton, such as naphthol, a substituted naphthol, or dihydroxynaphthalene, and the aldehyde compound is an aliphatic aldehyde or an aromatic aldehyde, 1 mol of the monomer with a phenolic hydroxy group is preferably allowed to react with 0.6 to 2 mol of the aldehyde compound in the presence of an acid catalyst at a temperature in the range of approximately 20° C. to 100° C.

In a modified product of the calixarene compound, a hydrogen atom of a hydroxy group in the resin is partly or entirely substituted with an acid dissociable protective group in such a manner as in the resin with a novolak phenolic hydroxy group.

In the (poly)vinyl resin or a modified product thereof (B4), for example, the (poly)vinyl resin is a homopolymer or copolymer of a compound selected from (poly)hydroxystyrene compounds, styrene, vinylnaphthalene, vinylanthracene, vinylcarbazole, indene, acenaphthylene, norbornene, cyclodecene, tetracyclododecene, nortricyclene, and (meth) acrylate monomers. For example, the polyhydroxystyrene compound is a compound represented by the following structural formula (14).

[Chem. 16]

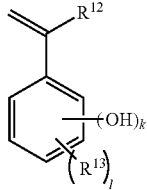

(14)

[wherein $R^{12}$ denotes a hydrogen atom, an alkyl group, a halogen atom, or a halogenated alkyl group; $R^{13}$ independently denotes an aliphatic hydrocarbon group, an aromatic hydrocarbon group, an alkoxy group, or a halogen atom; k denotes an integer in the range of 1 to 3; and l denotes an integer of 0 or 1 to 4.]

The (meth)acrylate monomers may preferably be various (meth)acrylate monomers exemplified as constituent monomers of the acrylic (meth)acrylate resin or a modified product thereof (B1-8) and (meth)acrylates with a cyclohexane ring or an adamantane structure.

In a modified product of the (poly)vinyl resin, a hydrogen atom of a hydroxy group in the (poly)vinyl resin may be partly or entirely substituted with an acid dissociable protective group. The hydroxy group is preferably a phenolic hydroxy group. Examples of the acid dissociable protective group include tertiary alkyl groups, alkoxyalkyl groups, acyl groups, alkoxycarbonyl groups, cyclic hydrocarbon groups containing a heteroatom, and trialkylsilyl groups. Examples of the tertiary alkyl groups include a t-butyl group and a t-pentyl group. Examples of the alkoxyalkyl groups include a methoxyethyl group, an ethoxyethyl group, a propoxyethyl group, a butoxyethyl group, a cyclohexyloxyethyl group, and a phenoxyethyl group. Examples of the acyl groups include an acetyl group, an ethanoyl group, a propanoyl group, a butanoyl group, a cyclohexanecarbonyl group, and a benzoyl group. Examples of the alkoxycarbonyl groups include a methoxycarbonyl group, an ethoxycarbonyl group, a propoxycarbonyl group, a butoxycarbonyl group, a cyclohexyloxycarbonyl group, and a phenoxycarbonyl group. Examples of the cyclic hydrocarbon groups containing a heteroatom include a tetrahydrofuranyl group and a tetrahydropyranyl group. Examples of the trialkylsilyl groups include a trimethylsilyl group, a triethylsilyl group, and a t-butyldimethylsilyl group. A hydrogen atom of a hydroxy group is partly or entirely substituted with an acid dissociable protective group, for example, by a reaction between the (poly)vinyl resin and a protective group introducing agent represented by one of the structural formulae (13-1) to (13-8).

The (poly)vinyl resin or a modified product thereof (B4) preferably has a mass-average molecular mass (Mw) in the range of 2,000 to 50,000. The (poly)vinyl resin or a modified product thereof (B4) preferably has a molecular weight distribution (Mw/Mn) in the range of 1.1 to 5.

The other resin with a phenolic hydroxy group or a modified product thereof (B5) refers to a resin with a phenolic hydroxy group having a molecular structure other than (B2) to (B4), may have any structure, and may be one widely known in electronic material applications. For example, the other resin with a phenolic hydroxy group is a dicyclopentadiene addition-type phenolic resin, a phenolic resin with an arylene dialkylene group, an alkoxyaryl-modified novolak resin, or an arylene ether type phenolic resin. In a modified product thereof, a hydrogen atom of a hydroxy group in the resin is partly or entirely substituted with an acid dissociable protective group in such a manner as in the resin with a novolak phenolic hydroxy group.

The resin component (B) is appropriately selected according to the desired application and may be used alone or in combination. For example, when a resist material according to the present invention is used in color resist applications, the resin component (B) is typically the active energy beam curing compound (B1). Among the resin component (B), the resin with a novolak phenolic hydroxy group or a modified product thereof (B2) is widely used in the g/i line, the (poly)hydroxystyrene resin (B4) is widely used in KrF excimer laser, and the active energy beam curing compound (B1) is widely used in ArF patterning applications. The resin with a novolak phenolic hydroxy group or a modified product thereof (B2), the calixarene compound or a modified product thereof (B3), or the other resin with a phenolic hydroxy group or a modified product thereof (B5), together with an epoxy resin, a melamine resin, or a glycoluril compound, has very high heat resistance as a thermosetting composition in resist underlayer film applications.

Depending on its specific use, a resist material according to the present invention may contain a component other than the calixarene compound (A) and the resin component (B). In a resist material according to the present invention, the amounts of the calixarene compound (A), the resin component (B), and the other component depend on the desired performance, application, and the like. In particular, to achieve the advantages of the present invention, for example, high smoothness and uniformity of films and high patterning performance, such as resolution, the amount of the calixarene compound (A) to be added preferably ranges from 0.005% to 1% by mass of the total mass of components of the resist material other than the organic solvent (the resin solid content).

The other component may be any traditional compound contained in typical resist materials. Although some specific examples of the other component are described below, a resist material according to the present invention is not limited to these examples.

As described above, when a resist material according to the present invention is used in color resist applications, the resin component (B) is typically the active energy beam curing compound (B1). A color resist material typically further contains a colorant, a polymerization initiator, and an organic solvent and optionally contains an ultraviolet absorber, an antioxidant, a photosensitizer, a silicone additive agent, a silane coupling agent, a fluorinated additive agent other than the calixarene compound (A), a rheology controlling agent, a defoaming agent, an antistatic agent, an anti-fogging agent, an adhesion aid, organic filler, and inorganic filler.

The colorant may be a known coloring material, for example, a red coloring material, such as a diketopyrrolopyrrole pigment or an anionic red organic dye; a green coloring material, such as a halogenated copper phthalocyanine pigment, a phthalocyanine green dye, a phthalocyanine blue dye, or an azo yellow organic dye; a blue coloring material, such as an E copper phthalocyanine pigment or a cationic blue organic dye; or a black coloring material, such as carbon black or a mixed black pigment. Instead of these, quantum dots (QDs) that emit light with a desired color tone may be used.

The polymerization initiator can be appropriately chosen according to the type of active energy beam to be emitted and the like. The polymerization initiator may be used in combination with a photosensitizer, such as an amine compound, a urea compound, a sulfur-containing compound, a phosphorus-containing compound, a chlorine-containing compound, or a nitrile compound. Specific examples of the polymerization initiator include alkylphenone polymerization initiators, such as 1-hydroxy-cyclohexyl-phenyl-ketone, 2-benzyl-2-dimethylamino-1-(4-morpholinophenyl)-butanone-1, and 2-(dimethylamino)-2-[(4-methylphenyl)methyl]-1-[4-(4-morpholinyl)phenyl]-1-butanone; acylphosphine oxide polymerization initiators, such as 2,4,6-trimethylbenzoyl-diphenyl-phosphine oxide; and intramolecular hydrogen abstraction type polymerization initiators, such as benzophenone compounds. These may be used alone or in combination.

Examples of commercial products of the polymerization initiator include "IRGACURE 127", "IRGACURE 184", "IRGACURE 250", "IRGACURE 270", "IRGACURE 290", "IRGACURE 369E", "IRGACURE 379EG", "IRGACURE 500", "IRGACURE 651", "IRGACURE 754", "IRGACURE 819", "IRGACURE 907", "IRGACURE 1173", "IRGACURE 2959", "IRGACURE MBF", "IRGACURE TPO", "IRGACURE OXE 01", and "IRGACURE OXE 02", each manufactured by BASF.

The amount of the polymerization initiator to be used preferably ranges from 0.01 to 15 parts by mass, more preferably 0.05 to 10 parts by mass, per 100 parts by mass of the active energy beam curing compound (B1).

The organic solvent may be any organic solvent. Specific examples of the organic solvent include alkyl monoalcohol solvents, such as methanol, ethanol, and propanol; alkyl polyol solvents, such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol), and glycerin; alkylene glycol monoalkyl ether solvents, such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, ethylene glycol monophenyl ether, and propylene glycol monomethyl ether; dialkylene glycol dialkyl ether solvents, such as diethylene glycol dimethyl ether, diethylene glycol diethyl ether, diethylene glycol dipropyl ether, and diethylene glycol dibutyl ether; alkylene glycol alkyl ether acetate solvents, such as ethylene glycol monomethyl ether acetate, ethylene glycol monoethyl ether acetate, and propylene glycol monomethyl ether acetate; cyclic ether solvents, such as 1,3-dioxane, 1,4-dioxane, tetrahydrofuran, and cyclopentylmethyl ether; ketone solvents, such as acetone, methyl ethyl ketone, methyl isobutyl ketone, cyclohexanone, and methyl amyl ketone; ester solvents, such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, and ethyl acetoacetate; and aromatic hydrocarbon solvents, such as benzene, toluene, and xylene.

A resist material according to the present invention for use in positive resist applications typically contains at least one of the resin with a novolak phenolic hydroxy group or a modified product thereof (B2), the (poly)vinyl resin or a modified product thereof (B4), and the other resin with a phenolic hydroxy group or a modified product thereof (B5) as the resin component (B), a photosensitizing agent or an acid generator, and an organic solvent. A positive resist material may further contain a silicone additive agent, a silane coupling agent, and a fluorinated additive agent other than the calixarene compound (A).

For example, the photosensitizing agent is a compound with a quinone diazide group. Specific examples of the compound with a quinone diazide group include complete ester compounds, partial ester compounds, amides, and partial amides between an aromatic (poly)hydroxy compound and a sulfonic acid with a quinone diazide group, such as naphthoquinone-1,2-diazido-5-sulfonic acid, naphthoquinone-1,2-diazido-4-sulfonic acid, or ortho-anthraquinone diazido sulfonic acid.

Examples of the aromatic (poly)hydroxy compound include polyhydroxybenzophenone compounds, such as 2,3,4-trihydroxybenzophenone, 2,4,4'-trihydroxybenzophenone, 2,4,6-trihydroxybenzophenone, 2,3,6-trihydroxybenzophenone, 2,3,4-trihydroxy-2'-methylbenzophenone, 2,3,4,4'-tetrahydroxybenzophenone, 2,2',4,4'-tetrahydroxybenzophenone, 2,3',4,4',6-pentahydroxybenzophenone, 2,2',3,4,4'-pentahydroxybenzophenone, 2,2',3,4,5-pentahydroxybenzophenone, 2,3',4,4',5',6-hexahydroxybenzophenone, and 2,3,3',4,4',5'-hexahydroxybenzophenone;

bis[(poly)hydroxyphenyl]alkane compounds, such as bis(2,4-dihydroxyphenyl)methane, bis(2,3,4-trihydroxyphenyl)methane, 2-(4-hydroxyphenyl)-2-(4'-hydroxyphenyl)propane, 2-(2,4-dihydroxyphenyl)-2-(2',4'-dihydroxyphenyl)propane, 2-(2,3,4-trihydroxyphenyl)-2-

(2',3',4'-trihydroxyphenyl)propane, 4,4'-{1-[4-[2-(4-hydroxyphenyl)-2-propyl]phenyl]ethylidene}bisphenol, and 3,3'-dimethyl-{1-[4-[2-(3-methyl-4-hydroxyphenyl)-2-propyl]phenyl]ethylidene}bisphenol;

tris(hydroxyphenyl)methane compounds and their methyl substitution products, such as tris(4-hydroxyphenyl)methane, bis(4-hydroxy-3,5-dimethylphenyl)-4-hydroxyphenylmethane, bis(4-hydroxy-2,5-dimethylphenyl)-4-hydroxyphenylmethane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-2,5-dimethylphenyl)-3,4-dihydroxyphenylmethane, and bis(4-hydroxy-3,5-dimethylphenyl)-3,4-dihydroxyphenylmethane; and bis(cyclohexylhydroxyphenyl) (hydroxyphenyl)methane compounds and their methyl substitution products, such as bis(3-cyclohexyl-4-hydroxyphenyl)-3-hydroxyphenylmethane, bis(3-cyclohexyl-4-hydroxyphenyl)-2-hydroxyphenylmethane, bis(3-cyclohexyl-4-hydroxyphenyl)-4-hydroxyphenylmethane, bis(5-cyclohexyl-4-hydroxy-2-methylphenyl)-2-hydroxyphenylmethane, bis(5-cyclohexyl-4-hydroxy-2-methylphenyl)-3-hydroxyphenylmethane, bis(5-cyclohexyl-4-hydroxy-2-methylphenyl)-4-hydroxyphenylmethane, bis(3-cyclohexyl-2-hydroxyphenyl)-3-hydroxyphenylmethane, bis(5-cyclohexyl-4-hydroxy-3-methylphenyl)-4-hydroxyphenylmethane, bis(5-cyclohexyl-4-hydroxy-3-methylphenyl)-3-hydroxyphenylmethane, bis(5-cyclohexyl-4-hydroxy-3-methylphenyl)-2-hydroxyphenylmethane, bis(3-cyclohexyl-2-hydroxyphenyl)-4-hydroxyphenylmethane, bis(3-cyclohexyl-2-hydroxyphenyl)-2-hydroxyphenylmethane, bis(5-cyclohexyl-2-hydroxy-4-methylphenyl)-2-hydroxyphenylmethane, and bis(5-cyclohexyl-2-hydroxy-4-methylphenyl)-4-hydroxyphenylmethane. These photosensitizing agents may be used alone or in combination.

The amount of photosensitizing agent in the positive resist material preferably ranges from 5 to 50 parts by mass per 100 parts by mass of the total resin solid content.

Examples of the photoacid generator include organic halides, sulfonates, onium salts, diazonium salts, and disulfone compounds, which may be used alone or in combination. Specific examples of these include s-triazine derivatives with a haloalkyl group, such as tris(trichloromethyl)-s-triazine, tris(tribromomethyl)-s-triazine, tris(dibromomethyl)-s-triazine, and 2,4-bis(tribromomethyl)-6-p-methoxyphenyl-s-triazine;

halogen substituted paraffinic hydrocarbon compounds, such as 1,2,3,4-tetrabromobutane, 1,1,2,2-tetrabromoethane, carbon tetrabromide, and iodo form; halogen substituted cycloparaffinic hydrocarbon compounds, such as hexabromocyclohexane, hexachlorocyclohexane, and hexabromocyclododecane;

benzene derivatives with a haloalkyl group, such as bis(trichloromethyl)benzene and bis(tribromomethyl)benzene; sulfone compounds with a haloalkyl group, such as tribromomethyl phenyl sulfone and trichloromethyl phenyl sulfone; sulfolane compounds with a halogen, such as 2,3-dibromosulfolane; isocyanurate compounds with a haloalkyl group, such as tris(2,3-dibromopropyl)isocyanurate;

sulfonium salts, such as triphenylsulfonium chloride, triphenylsulfonium methane sulfonate, triphenylsulfonium trifluoromethane sulfonate, diphenyl(4-methylphenyl)sulfonium trifluoromethane sulfonate, triphenylsulfonium p-toluene sulfonate, triphenylsulfonium tetrafluoroborate, triphenylsulfonium hexafluoroarsenate, and triphenylsulfonium hexafluorophosphonate;

iodonium salts, such as diphenyliodonium trifluoromethane sulfonate, diphenyliodonium p-toluene sulfonate, diphenyliodonium tetrafluoroborate, diphenyliodonium hexafluoroarsenate, and diphenyliodonium hexafluorophosphonate;

sulfonate compounds, methyl p-toluenesulfonate, ethyl p-toluenesulfonate, butyl p-toluenesulfonate, phenyl p-toluenesulfonate, 1,2,3-tris(p-toluenesulfonyloxy)benzene, benzoin p-toluenesulfonate, methyl methanesulfonate, ethyl methanesulfonate, butyl methanesulfonate, 1,2,3-tris(methanesulfonyloxy)benzene, phenyl methanesulfonate, benzoin methanesulfonate, methyl trifluoromethanesulfonate, ethyl trifluoromethanesulfonate, butyl trifluoromethanesulfonate, 1,2,3-tris(trifluoromethanesulfonyloxy)benzene, phenyl trifluoromethanesulfonate, and benzoin trifluoromethanesulfonate; disulfone compounds, such as diphenyl disulfone;

diazido sulfone compounds, such as bis(phenylsulfonyl)diazomethane, bis(2,4-dimethylphenylsulfonyl)diazomethane, bis(cyclohexylsulfonyl)diazomethane, cyclohexylsulfonyl-(2-methoxyphenylsulfonyl)diazomethane, cyclohexylsulfonyl-(3-methoxyphenylsulfonyl)diazomethane, cyclohexylsulfonyl-(4-methoxyphenylsulfonyl)diazomethane, cyclopentylsulfonyl-(2-methoxyphenylsulfonyl)diazomethane, cyclopentylsulfonyl-(3-methoxyphenylsulfonyl)diazomethane, cyclopentylsulfonyl-(4-methoxyphenylsulfonyl)diazomethane, cyclohexylsulfonyl-(2-fluorophenylsulfonyl)diazomethane, cyclohexylsulfonyl-(3-fluorophenylsulfonyl)diazomethane, cyclohexylsulfonyl-(4-fluorophenylsulfonyl)diazomethane, cyclopentylsulfonyl-(2-fluorophenylsulfonyl)diazomethane, cyclopentylsulfonyl-(3-fluorophenylsulfonyl)diazomethane, cyclopentylsulfonyl-(4-fluorophenylsulfonyl)diazomethane, cyclohexylsulfonyl-(2-chlorophenylsulfonyl)diazomethane, cyclohexylsulfonyl-(3-chlorophenylsulfonyl)diazomethane, cyclohexylsulfonyl-(4-chlorophenylsulfonyl)diazomethane, cyclopentylsulfonyl-(2-chlorophenylsulfonyl)diazomethane, cyclopentylsulfonyl-(3-chlorophenylsulfonyl)diazomethane, cyclopentylsulfonyl-(4-chlorophenylsulfonyl)diazomethane, cyclohexylsulfonyl-(2-trifluoromethylphenylsulfonyl)diazomethane, cyclohexylsulfonyl-(3-trifluoromethylphenylsulfonyl)diazomethane, cyclohexylsulfonyl-(4-trifluoromethylphenylsulfonyl)diazomethane, cyclopentylsulfonyl-(2-trifluoromethylphenylsulfonyl)diazomethane, cyclopentylsulfonyl-(3-trifluoromethylphenylsulfonyl)diazomethane, cyclopentylsulfonyl-(4-trifluoromethylphenylsulfonyl)diazomethane, cyclohexylsulfonyl-(2-trifluoromethoxyphenylsulfonyl)diazomethane, cyclohexylsulfonyl-(3-trifluoromethoxyphenylsulfonyl)diazomethane, cyclohexylsulfonyl-(4-trifluoromethoxyphenylsulfonyl)diazomethane, cyclopentylsulfonyl-(2-trifluoromethoxyphenylsulfonyl)diazomethane, cyclopentylsulfonyl-(3-trifluoromethoxyphenylsulfonyl)diazomethane, cyclopentylsulfonyl-(4-trifluoromethoxyphenylsulfonyl)diazomethane, cyclohexylsulfonyl-(2,4,6-trimethylphenylsulfonyl)diazomethane, cyclohexylsulfonyl-(2,3,4-trimethylphenylsulfonyl)diazomethane, cyclohexylsulfonyl-(2,4,6-triethylphenylsulfonyl)diazomethane, cyclohexylsulfonyl-(2,3,4-triethylphenylsulfonyl)diazomethane, cyclopentylsulfonyl-(2,4,6-trimethylphenylsulfonyl)diazomethane, cyclopentylsulfonyl-(2,3,4-trimethylphenylsulfonyl)diazomethane, cyclopentylsulfonyl-(2,4,6-triethylphenylsulfonyl)diazomethane, cyclopentylsulfonyl-(2,3,4-triethylphenylsulfonyl)diazomethane, phenylsulfonyl-(2-methoxyphenylsulfonyl)diazomethane, phenylsulfonyl-(3-methoxyphenylsulfonyl)diazomethane, phenylsulfonyl-(4- methoxyphenylsulfonyl)diazomethane, bis(2-methoxyphenylsulfonyl)diazomethane, bis(3-methoxyphenylsulfonyl)diazomethane, bis(4-methoxyphenylsulfonyl)diazomethane, phenylsulfonyl-(2,4,6-trimethylphenylsulfonyl)diazomethane, phenylsulfonyl-(2,3,4-trimethylphenylsulfonyl)diazomethane, phenylsulfonyl-(2,4,6-triethylphenylsulfonyl)diazomethane, phenylsulfonyl-(2,3,4-triethylphenylsulfonyl)diazomethane, 2,4-dimethylphenylsulfonyl-(2,4,6-trimethylphenylsulfonyl)diazomethane, 2,4-dimethylphenylsulfonyl-(2,3,4-trimethylphenylsulfonyl)diazomethane, phenylsulfonyl-(2-fluorophenylsulfonyl)diazomethane, phenylsulfonyl-(3-fluorophenylsulfonyl)diazomethane, and phenylsulfonyl-(4-fluorophenylsulfonyl)diazomethane;

o-nitrobenzyl ester compounds, such as o-nitrobenzyl-p-toluene sulfonate; and sulfonyl hydrazide compounds, such as N,N'-di(phenylsulfonyl)hydrazide.

To provide a positive resist material with high photosensitivity, the amount of photoacid generator to be added preferably ranges from 0.1 to 20 parts by mass per 100 parts by mass of the resin solid content.

The positive resist material may contain an organic basic compound to neutralize an acid produced from the photoacid generator upon exposure to light. The addition of the organic basic compound is effective in preventing variations in the dimensions of a resist pattern caused by a movement of an acid produced from the photoacid generator. Examples of the organic basic compound to be used here include organic amine compounds selected from nitrogen-containing compounds, more specifically, pyrimidine compounds, such as pyrimidine, 2-aminopyrimidine, 4-aminopyrimidine, 5-aminopyrimidine, 2,4-diaminopyrimidine, 2,5-diaminopyrimidine, 4,5-diaminopyrimidine, 4,6-diaminopyrimidine, 2,4,5-triaminopyrimidine, 2,4,6-triaminopyrimidine, 4,5,6-triaminopyrimidine, 2,4,5,6-tetraaminopyrimidine, 2-hydroxypyrimidine, 4-hydroxypyrimidine, 5-hydroxypyrimidine, 2,4-dihydroxypyrimidine, 2,5-dihydroxypyrimidine, 4,5-dihydroxypyrimidine, 4,6-dihydroxypyrimidine, 2,4,5-trihydroxypyrimidine, 2,4,6-trihydroxypyrimidine, 4,5,6-trihydroxypyrimidine, 2,4,5,6-tetrahydroxypyrimidine, 2-amino-4-hydroxypyrimidine, 2-amino-5-hydroxypyrimidine, 2-amino-4,5-dihydroxypyrimidine, 2-amino-4,6-dihydroxypyrimidine, 4-amino-2,5-dihydroxypyrimidine, 4-amino-2,6-dihydroxypyrimidine, 2-amino-4-methylpyrimidine, 2-amino-5-methylpyrimidine, 2-amino-4,5-dimethylpyrimidine, 2-amino-4,6-dimethylpyrimidine, 4-amino-2,5-dimethylpyrimidine, 4-amino-2,6-dimethylpyrimidine, 2-amino-4-methoxypyrimidine, 2-amino-5-methoxypyrimidine, 2-amino-4,5-dimethoxypyrimidine, 2-amino-4,6-dimethoxypyrimidine, 4-amino-2,5-dimethoxypyrimidine, 4-amino-2,6-dimethoxypyrimidine, 2-hydroxy-4-methylpyrimidine, 2-hydroxy-5-methylpyrimidine, 2-hydroxy-4,5-dimethylpyrimidine, 2-hydroxy-4,6-dimethylpyrimidine, 4-hydroxy-2,5-dimethylpyrimidine, 4-hydroxy-2,6-dimethylpyrimidine, 2-hydroxy-4-methoxypyrimidine, 2-hydroxy-4-methoxypyrimidine, 2-hydroxy-5-methoxypyrimidine, 2-hydroxy-4,5-dimethoxypyrimidine, 2-hydroxy-4,6-dimethoxypyrimidine, 4-hydroxy-2,5-dimethoxypyrimidine, and 4-hydroxy-2,6-dimethoxypyrimidine;

pyridine compounds, such as pyridine, 4-dimethylaminopyridine, and 2,6-dimethylpyridine;

amine compounds substituted with a hydroxyalkyl group having 1 to 4 carbon atoms, such as diethanolamine, triethanolamine, triisopropanolamine, tris(hydroxymethyl) aminomethane, and bis(2-hydroxyethyl)imino tris(hydroxymethyl)methane; and aminophenol compounds, such as 2-aminophenol, 3-aminophenol, and 4-aminophenol. These may be used alone or in combination. In particular, in terms of the dimensional stability of resist patterns upon exposure to light, preferred are the pyrimidine compounds, pyridine compounds, or amine compounds with a hydroxy group, particularly amine compounds with a hydroxy group.

The amount of the organic basic compound, if present, preferably ranges from 0.1% to 100% by mole, more preferably 1% to 50% by mole, of the photoacid generator content.

Examples of the organic solvent include, but are not limited to, alkylene glycol monoalkyl ethers, such as ethylene glycol monomethyl ether, ethylene glycol monoethyl ether, ethylene glycol monopropyl ether, and ethylene glycol monobutyl ether propylene glycol monomethyl ether; dialkylene glycol dialkyl ethers, such as diethylene glycol dimethyl ether, diethylene glycol diethyl ether, diethylene glycol dipropyl ether, and diethylene glycol dibutyl ether; alkylene glycol alkyl ether acetates, such as ethylene glycol monomethyl ether acetate, ethylene glycol monoethyl ether acetate, and propylene glycol monomethyl ether acetate; ketone compounds, such as acetone, methyl ethyl ketone, cyclohexanone, and methyl amyl ketone; cyclic ethers, such as dioxane; and ester compounds, such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, and ethyl acetoacetate, which may be used alone or in combination.

A resist material according to the present invention for use in resist underlayer film (BARC) applications typically contains the resin component (B), a curing agent that can cause a curing reaction, a photosensitizing agent, and an organic solvent as described above. When the resin component (B) has a hydroxy group or a carboxy group protected by an acid dissociable protective group, a photoacid generator is preferably also used. The resist material may further contain an antioxidant, a photosensitizer, a silicone additive agent, a silane coupling agent, a fluorinated additive agent other than the calixarene compound (A), a rheology controlling agent, a defoaming agent, an antistatic agent, an anti-fogging agent, an adhesion aid, organic filler, inorganic filler, and the like.

Examples of the curing agent include melamine compounds, guanamine compounds, glycoluril compounds, urea compounds, resole resins, epoxy compounds, isocyanate compounds, azide compounds, compounds with a double bond, such as with an alkenyl ether group, acid anhydrides, and oxazoline compounds.

Examples of the photosensitizing agent include complete ester compounds, partial ester compounds, amides, and partial amides between an aromatic (poly)hydroxy compound and a sulfonic acid with a quinone diazide group, such as 1,2-naphthoquinone-2-diazido-5-sulfonic acid, or a halide thereof.

Examples of the photoacid generator include organic halides, sulfonates, onium salts, diazonium salts, and disulfone compounds, which may be used alone or in combination.

EXAMPLES

Although the present invention is more specifically described in the following production examples and examples, the present invention is not limited to these examples. Unless otherwise specified, parts and % in the examples are based on mass.

In the examples, the molecular weight of resin was measured with a gel permeation chromatograph (GPC) under the following conditions.

Measuring apparatus: HLC-8220 manufactured by Tosoh Corporation

Column: guard column $H_{XL}$-H manufactured by Tosoh Corporation

+TSKgel G5000HXL manufactured by Tosoh Corporation

+TSKgel G4000HXL manufactured by Tosoh Corporation

+TSKgel G3000HXL manufactured by Tosoh Corporation

+TSKgel G2000HXL manufactured by Tosoh Corporation

Detector: differential refractometer (RI)

Data processing: SC-8010 manufactured by Tosoh Corporation

Measurement conditions: Column temperature 40° C.

Solvent tetrahydrofuran

Flow rate 1.0 ml/min

Reference: polystyrene

Sample: A tetrahydrofuran solution with a resin solid content of 0.4% by mass passed through a microfilter (100 μl).

$^1$H-NMR was measured with "JNM-ECM400S" manufactured by JEOL RESONANCE under the following conditions.

Magnetic field strength: 400 MHz

Number of scans: 16

Solvent: deuterated chloroform

Sample concentration: 2 mg/0.5 ml $^{13}$C-NMR was measured with "JNM-ECM400S" manufactured by JEOL RESONANCE under the following conditions.

Magnetic field strength: 100 MHz

Number of scans: 1000

Solvent: deuterated chloroform

Sample concentration: 2 mg/0.5 ml $^{19}$F-NMR was measured with "JNM-ECM400S" manufactured by JEOL RESONANCE under the following conditions.

Magnetic field strength: 400 MHz

Number of scans: 16

Solvent: deuterated chloroform

Sample concentration: 2 mg/0.5 ml

FD-MS was measured with "JMS-T100GC AccuTOF" manufactured by JEOL Ltd. under the following conditions.

Measurement range: m/z=50.00 to 2000.00

Rate of change: 25.6 mA/min

Final current value: 40 mA

Cathode voltage: −10 kV

Production Example 1 Production of Calixarene Compound (A-1)

<Production of Intermediate (1)>

50 g of tert-butyl calix[4]arene represented by the following structural formula (a), 32.26 g of phenol, and 350 ml of anhydrous toluene were charged into a 1-liter four-neck flask equipped with a stirrer, a thermometer, and a reflux condenser tube and were stirred at 300 rpm in a nitrogen flow environment. The tert-butyl calix[4]arene was not dissolved but was suspended. While the flask was placed in an ice bath, 51.37 g of anhydrous aluminum (III) chloride was added in portions. The solution color changed to clear pale orange, and anhydrous aluminum (III) chloride was precipitated on the bottom. After stirring at room temperature for 5 hours, the reaction mixture was transferred into a 1-L beaker, and ice, 100 ml of 1 N hydrochloric acid, and 350 ml of toluene were added to terminate the reaction. The solution color changed to clear light yellow. The reaction mixture was transferred to a separatory funnel, and the organic phase was collected. 100 ml of toluene was added to the aqueous phase to extract organic components three times. The extract was mixed with the collected organic phase. The organic phase was dried over anhydrous magnesium sulfate and was then filtered to collect the organic phase. The solvent was evaporated with an evaporator, and a mixture of white crystals and clear colorless liquid was obtained. Methanol was slowly added to the mixture while stirring to reprecipitate the product from the liquid. White crystals were filtered off with a Kiriyama Rohto (funnel), were washed with methanol, and were dried under vacuum. 29.21 g of an intermediate (1) represented by the following structural formula (b) was obtained.

[Chem. 17]

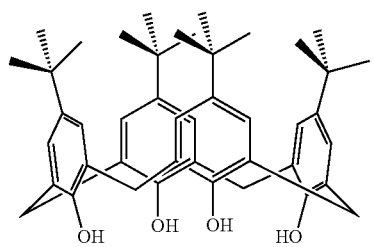

(a)

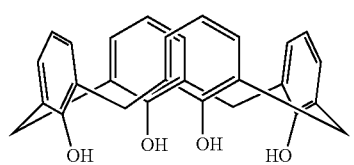

(b)

<Allyl Etherification of Intermediate (1)>

16.41 g of the intermediate (1), 65.64 ml of anhydrous N,N-dimethylformamide, and 37.87 g of 49% aqueous sodium hydroxide were charged into a 1-liter four-neck flask equipped with a stirrer, a thermometer, a dropping funnel, and a reflux condenser tube and were stirred at 300 rpm in a nitrogen flow environment. The solution was clear light yellow. 56.13 g of allyl bromide was added dropwise from a dropping funnel at room temperature for 30 minutes. 30 minutes after the completion of the dropwise addition, a milk white solid was precipitated as slurry. After reaction for another 2 hours, acetic acid and pure water were slowly added to terminate the reaction. Crystals were filtered off with a Kiriyama Rohto (funnel), were washed with methanol, and were then dried under vacuum. 17.94 g of an allyl etherification product of the intermediate (1) was obtained.

<Production of Intermediate (2)>

14.69 g of the allyl etherification product of the intermediate (1) and 58.76 g of N,N-dimethylaniline were charged into a 1-liter four-neck flask equipped with a stirrer, a thermometer, and a reflux condenser tube and were stirred at 300 rpm in a nitrogen flow environment. The mixture was heated to reflux and was stirred for 3 hours. The reaction mixture was cooled to room temperature and was then transferred to a beaker. Ice and 20 g of chloroform were added to the reaction mixture. While the beaker was placed in an ice bath, 48.04 g of 38% concentrated hydrochloric acid was slowly added, and the solution turned to clear light yellow. The reaction mixture was transferred to a separatory funnel, and the organic phase was collected. 20 g of chloroform was added to the aqueous phase to extract organic components three times. The extract was mixed with the collected organic phase. The organic phase was dried over anhydrous magnesium sulfate and was then filtered to collect the organic phase. The solvent was evaporated with an evaporator, and a mixture of white crystals and clear light green liquid was obtained. Methanol was slowly added to the mixture to reprecipitate the product from the liquid. White crystals were filtered off with a Kiriyama Rohto (funnel), were washed with methanol, and were dried under vacuum. 12.77 g of an intermediate (2) represented by the following structural formula (c) was obtained.

[Chem. 18]

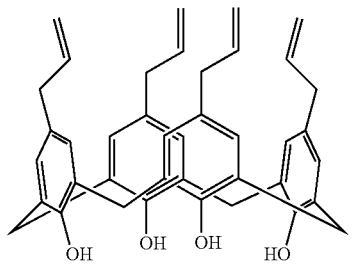

(c)

<Introduction of Perfluoroalkyl Group>

10.00 g of the intermediate (2), 1.70 g of 2,2'-azobis(2,4-dimethylvaleronitrile (manufactured by Wako Pure Chemical Industries, Ltd.), 31.5 ml of anhydrous toluene, and 52.02 g of 1,1,2,2-tetrahydroperfluorooctanethiol were charged into a 1-liter four-neck flask equipped with a stirrer, a thermometer, and a reflux condenser tube and were stirred at 300 rpm in a nitrogen flow environment. The mixture was heated to 65° C. and was allowed to react for 12 hours. The reaction mixture was cooled to room temperature and was then transferred to a separatory funnel. 30 g of 1 N aqueous sodium hydrogen carbonate and 30 g of chloroform were added to the reaction mixture to separate the organic phase. 20 g of chloroform was added to the aqueous phase to extract organic components three times. The extract was mixed with the collected organic phase. The organic phase was washed with 1 N aqueous sodium hydroxide, was dried over anhydrous magnesium sulfate, and was filtered. The solvent was evaporated with an evaporator. The resulting clear red liquid was cooled with ice, and methanol was added to the liquid to reprecipitate crystals. Gray crystals were filtered off with a Kiriyama Rohto (funnel), were washed with methanol, and were dried under vacuum. 31.08 g of a calixarene compound (A-1) represented by the following structural formula (d) was obtained.

[Chem. 19]

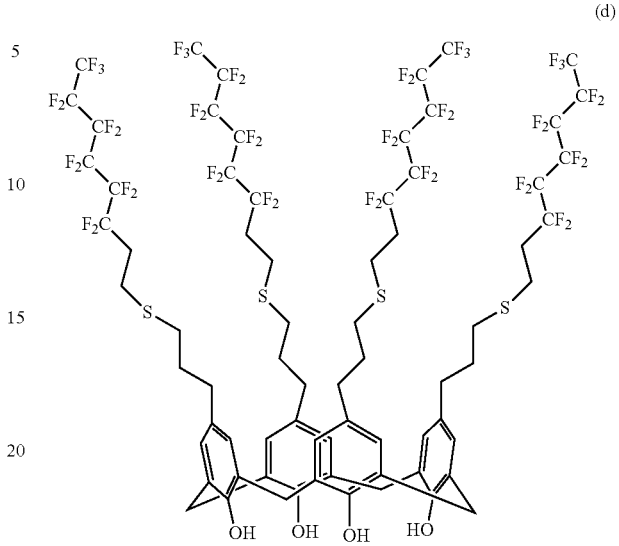

(d)

Production Example 2 Production of Novolak Phenolic Resin (B2-1)

A four-neck flask equipped with a stirrer and a thermometer was charged with 1620 parts by mass of m-cresol, 1080 parts by mass of p-cresol, 6.3 parts by mass of oxalic acid, and 1230 parts by mass of 42% formaldehyde. The mixture was allowed to react at 100° C. and was heated to 200° C. at atmospheric pressure for dehydration and distillation. The mixture was further heated to 230° C. for vacuum distillation for 6 hours. 1840 parts by mass of a novolak phenolic resin (B2-1) was obtained. The novolak phenolic resin (B2-1) had a number-average molecular weight (Mn) of 1,526, a mass-average molecular mass (Mw) of 12,048, and a molecular weight distribution (Mw/Mn) of 7.90.

Comparative Production Example 1 Production of Fluorinated Surfactant (A')

A glass flask equipped with a stirrer, a thermometer, a condenser tube, and a dropping apparatus was charged with 20 parts by mass of a perfluoropolyether compound represented by the following formula (a), 20 parts by mass of diisopropyl ether, 0.02 parts by mass of p-methoxyphenol, and 3.1 parts by mass of triethylamine. Stirring was started in the airflow. While the flask was kept at 10° C., 2.7 parts by mass of acryloyl chloride was added dropwise for 1 hour. After the completion of the dropwise addition, the mixture was stirred at 10° C. for 1 hour, at 30° C. for 1 hour, and at 50° C. for 10 hours and was checked for the absence of acryloyl chloride by gas chromatography. 40 parts by mass of diisopropyl ether and 80 parts by mass of ion-exchanged water were added to the mixture, which was then left standing to separate an aqueous layer. The same washing with water was performed three times, and then 0.02 parts by mass of p-methoxyphenol and 8 parts by mass of magnesium sulfate were added to the mixture, which was then left standing for 1 day. The magnesium sulfate was filtered off, and the solvent was evaporated under reduced pressure. A diacrylate compound of a perfluoropolyether compound represented by the following formula (a) was obtained.

[Chem. 20]

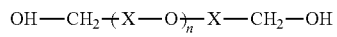

(a)

[wherein n denotes an integer; X denotes a perfluoromethylene group or a perfluoroethylene group; the average number of perfluoromethylene groups per molecule is 7, the average number of perfluoroethylene groups per molecule is 8, and the average number of fluorine atoms per molecule is 46; and the number-average molecular weight (Mn) is 1,500.]

A glass flask equipped with a stirrer, a thermometer, a condenser tube, and a dropping apparatus was charged with 63 parts by mass of methyl isobutyl ketone, which was then heated to 105° C. in a nitrogen stream with stirring. Three liquids, that is, 21.5 parts by mass of the diacrylate compound, 41.3 parts by mass of 2-hydroxyethyl methacrylate, and a mixed solution of 9.4 parts by mass of t-butyl peroxy-2-ethylhexanoate and 126 parts by mass of methyl isobutyl ketone (135.4 parts by mass in total) in different dropping apparatuses were then added dropwise for 2 hours while the flask was kept at 105° C. After the completion of the dropwise addition, the mixture was stirred at 105° C. for another 10 hours, and the solvent was evaporated under reduced pressure. A polymer (1) was obtained. 74.7 parts by mass of methyl ethyl ketone, 0.1 parts by mass of p-methoxyphenol, and 0.06 parts by mass of dibutyltin dilaurate were added, and stirring was started in the airflow. 44.8 parts by mass of 2-acryloyloxyethyl isocyanate was added dropwise at 60° C. for 1 hour. After the completion of the dropwise addition, the mixture was stirred at 60° C. for another 1 hour. After the mixture was stirred at 80° C. for 10 hours, the absence of the isocyanate group was confirmed by IR spectrum measurement. After 37.4 parts by mass of methyl ethyl ketone was added, the reaction mixture was filtered, and a 50% by mass methyl ethyl ketone solution of a fluorinated surfactant (A') was obtained. While the methyl ethyl ketone was evaporated under reduced pressure, propylene glycol monomethyl ether was added dropwise for solvent substitution. A 5% by mass propylene glycol monomethyl ether acetate solution of the fluorinated surfactant (A') was obtained. The fluorinated surfactant (A') had a number-average molecular weight (Mn) of 2,400, a weight-average molecular weight (Mw) of 7,100, and a molecular weight distribution (Mw/Mn) of 2.96.

Example 1 and Comparative Example 1 Production and Evaluation of Resist Materials Resist materials were prepared through the following procedure and were subjected to various evaluations. Table 1 shows the results.

40 parts by mass of the novolak phenolic resin (B2-1) was dissolved in 50 parts by mass of propylene glycol monomethyl ether acetate. The solution was mixed with 10 parts by mass of a photosensitizing agent (*1) and 3 parts by mass of a 5% by mass propylene glycol monomethyl ether acetate solution of the calixarene compound (A-1) and was filtered through a 0.2-μm cartridge filter. A resist material (1) was obtained.

40 parts by mass of the novolak phenolic resin (B2-1) was dissolved in 50 parts by mass of propylene glycol monomethyl ether acetate. The solution was mixed with 10 parts by mass of a photosensitizing agent (*1) and 3 parts by mass of a 5% by mass propylene glycol monomethyl ether acetate solution of the fluorinated surfactant (A') and was filtered through a 0.2-μm cartridge filter. A resist material (1') was obtained.

(*1) photosensitizing agent: "P-200", a condensate between 1 mol of 4,4'-[1-[4-[1-(4-hydroxyphenyl)-1-methylethyl]phenyl]ethylidene]bisphenol and 2 mol of 1,2-naphthoquinone-2-diazido-5-sulfonyl chloride, manufactured by Toyo Gosei Co., Ltd.

Evaluation of Film Uniformity (1)

The resist material (1) was applied with a spin coater to a 5-inch silicon wafer to a thickness of approximately 5 μm and was dried on a hot plate at 110° C. for 60 seconds to form a film. The surface of the film was observed with a sodium lamp to visually inspect for uneven application (roughness) and was rated according to the following criteria.

A: Few film irregularities were observed on the film surface.

B: Film irregularities were partly observed on the film surface.

C: Many film irregularities were observed on the film surface.

Evaluation of Film Uniformity (2)

The resist material (1) was applied with a spin coater to a 5-inch silicon wafer to a thickness of approximately 5 μm and was left standing at room temperature for 5 minutes. The resist material (1) was then dried on a hot plate at 110° C. for 60 seconds to form a film. The surface of the film was observed with a sodium lamp to visually inspect for tree-ring-like streaks and was rated according to the following criteria.

A: Less than 5 streaks were observed on the film surface.

B: 5 to 9 streaks were observed on the film surface.

C: 10 or more streaks were observed on the film surface.

Evaluation of Resolution

The resist material (1) was applied with a spin coater to a 5-inch silicon wafer to a thickness of approximately 2 μm and was dried on a hot plate at 110° C. for 60 seconds. The resist material (1) was irradiated with a ghi line at 200 mJ/cm² using an i-line contact mask aligner ("EVG610" manufactured by EVG) through a photomask and was then heated at 140° C. for 60 seconds. The resist material (1) was then immersed in an alkaline developer (2.38% aqueous tetramethylammonium hydroxide) for 60 seconds and was dried on a hot plate at 110° C. for 60 seconds. The pattern state was observed with a laser microscope ("VK-X200" manufactured by Keyence Corporation) and was rated A for a resolution of 1 μm for a L/S=1/1 linewidth and otherwise rated B.

TABLE 1

| | Example 1<br>Resist material (1) | Comparative example 1<br>Resist material (1') |
| --- | --- | --- |
| Film uniformity | A | B |
| Film smoothness | A | C |
| Resolution | A | B |

Reference Example Evaluation of Minimum Additive Amount

In the production of the resist material (1), 10 samples were prepared by changing the amount of 5% by mass propylene glycol monomethyl ether acetate solution of the calixarene compound (A-1) in the range of 1 to 10 parts by mass in increments of 1 part by mass. The samples were subjected to the evaluation test described in Evaluation of Film Uniformity (1). Consequently, the minimum amount of 5% by mass propylene glycol monomethyl ether acetate solution of the calixarene compound (A-1) for the rating A was 2 parts by mass.

In the production of the resist material (1'), 10 samples were prepared by changing the amount of 5% by mass propylene glycol monomethyl ether acetate solution of the fluorinated surfactant (A') in the range of 1 to 10 parts by mass in increments of 1 part by mass. The samples were subjected to the evaluation test described in Evaluation of Film Uniformity (1). Consequently, the minimum amount of 5% by mass propylene glycol monomethyl ether acetate solution of the fluorinated surfactant (A') for the rating A was 5 parts by mass.

The invention claimed is:

1. A resist material comprising: a calixarene compound (A) with a molecular structure represented by the following structural formula (1-1) or (1-2); and a resin component (B):

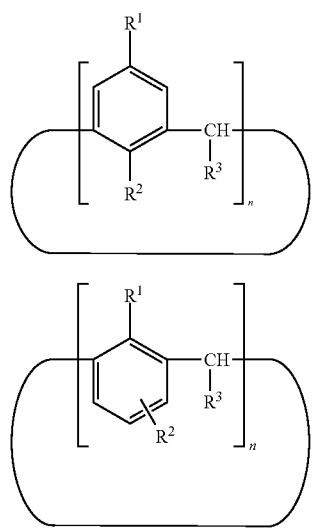

wherein $R^1$ denotes a perfluoroalkyl group or a structural moiety with a perfluoroalkyl group represented by —X—$R^F$, wherein $R^F$ denotes the perfluoroalkyl group and X is an alkylene group that optionally has a substituent, a (poly)alkylene ether structure, a (poly)alkylene thioether structure, a (poly)ester structure, a (poly)urethane structure, or a structural moiety composed thereof;
$R^2$ denotes a hydrogen atom, a polar group selected from a hydroxy group, an amino group, a carboxy group, a thiol group, a phosphate group, and an alkoxysilyl group, a polymerizable group selected from a vinyl group, a vinyloxy group, an ethynyl group, an ethynyloxy group, a (meth)acryloyl group, a (meth)acryloyloxy group, a (2-methyl)glycidyl group, a (2-methyl)glycidyloxy group, a 3-alkyloxetanylmethyl group, and a 3-alkyloxetanylmethyloxy group, or a structural moiety with the polar group or the polymerizable group; and
$R^3$ denotes a hydrogen atom, an aliphatic hydrocarbon group that optionally has a substituent, or an aryl group that optionally has a substituent; n denotes an integer in the range of 2 to 10.

2. The resist material according to claim 1, wherein the resin component (B) contains as an essential component an active energy beam curing compound (B1), a resin with a novolak phenolic hydroxy group or a modified product thereof (B2), a calixarene compound other than the calixarene compound (A) or a modified product thereof (B3), a (poly)hydroxystyrene resin (B4), or another resin with a phenolic hydroxy group or a modified product thereof (B5).

3. The resist material according to claim 1, wherein $R^2$ denotes the structural moiety with the polar group represented by one of the following structural formulae (3-1) to (3-7),

 (3-1)

 (3-2)

 (3-3)

 (3-4)

 (3-5)

 (3-6)

 (3-7)

wherein $R^4$ independently denotes an alkylene group having 1 to 6 carbon atoms, and $R^5$ denotes an alkyl group having 1 to 3 carbon atoms.

4. The resist material according to claim 1, wherein X is a (poly)alkylene ether chain or a (poly)alkylene thioether chain.

5. The resist material according to claim 4, wherein X has an alkylene group having 1 to 6 carbon atoms.

6. The resist material according to claim 1, wherein n is 4, 6, or 8.

7. The resist material according to claim 2, wherein $R^2$ denotes the structural moiety with the polar group represented by one of the following structural formulae (3-1) to (3-7),

 (3-1)

 (3-2)

 (3-3)

 (3-4)

 (3-5)

-continued

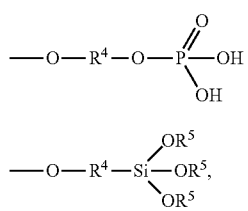

(3-6)

(3-7)

wherein $R^4$ independently denotes an alkylene group having 1 to 6 carbon atoms, and $R^5$ denotes an alkyl group having 1 to 3 carbon atoms.

8. The resist material according to claim 2, wherein X is a (poly)alkylene ether chain or a (poly)alkylene thioether chain.

9. The resist material according to claim 8, wherein X has an alkylene group having 1 to 6 carbon atoms.

10. The resist material according to claim 2, wherein n is 4, 6, or 8.

11. The resist material according to claim 1, wherein $R^2$ denotes a polymerizable group selected from a vinyl group, a vinyloxy group, an ethynyl group, an ethynyloxy group, a (meth)acryloyl group, a (meth)acryloyloxy group, a (2-methyl)glycidyl group, a (2-methyl)glycidyloxy group, a 3-alkyloxetanylmethyl group, and a 3-alkyloxetanylmethyloxy group, or a structural moiety with the polymerizable group.

12. The resist material according to claim 2, wherein $R^2$ denotes a polymerizable group selected from a vinyl group, a vinyloxy group, an ethynyl group, an ethynyloxy group, a (meth)acryloyl group, a (meth)acryloyloxy group, a (2-methyl)glycidyl group, a (2-methyl)glycidyloxy group, a 3-alkyloxetanylmethyl group, and a 3-alkyloxetanylmethyloxy group, or a structural moiety with the polymerizable group.

* * * * *